US010561161B2

(12) United States Patent
Fang et al.

(10) Patent No.: US 10,561,161 B2
(45) Date of Patent: *Feb. 18, 2020

(54) ENCAPSULATION SYSTEM FOR PROTECTION OF PROBIOTICS DURING PROCESSING

(71) Applicants: PepsiCo, Inc., Purchase, NY (US); Massey University, Palmerston North (NZ)

(72) Inventors: Yuan Fang, Cortlandt Manor, NY (US); Breda Kennedy, Ardmore (IE); Teodoro Rivera, Algonquin, IL (US); Kyoung-Sik Han, Palmerston North (NZ); Anil Kumar Anal, Bangkok (TH); Harjinder Singh, Palmerston North (NZ)

(73) Assignees: Pepsico, Inc., Purchase, NY (US); Massey University, Palmerston North (NZ)

( * ) Notice: Subject to any disclaimer, the term of this patent is extended or adjusted under 35 U.S.C. 154(b) by 137 days.

This patent is subject to a terminal disclaimer.

(21) Appl. No.: 15/694,015

(22) Filed: Sep. 1, 2017

(65) Prior Publication Data

US 2018/0084805 A1 Mar. 29, 2018

Related U.S. Application Data

(63) Continuation of application No. 13/088,165, filed on Apr. 15, 2011, now Pat. No. 9,788,563.

(51) Int. Cl.
*A23L 1/00* (2006.01)
*A23L 2/52* (2006.01)
(Continued)

(52) U.S. Cl.
CPC .................. *A23L 2/52* (2013.01); *A23L 2/02* (2013.01); *A23L 2/60* (2013.01); *A23L 2/66* (2013.01);
(Continued)

(58) Field of Classification Search
None
See application file for complete search history.

(56) References Cited

U.S. PATENT DOCUMENTS

| 2004/0146564 A1* | 7/2004 | Subirade | A61K 9/1658 424/499 |
| 2012/0156252 A1* | 6/2012 | Brodkorb | B01J 13/0065 424/400 |

* cited by examiner

*Primary Examiner* — Tamra L. Dicus
(74) *Attorney, Agent, or Firm* — Barnes & Thornburg LLP; G. Peter Nichols

(57) ABSTRACT

Comestible products, for example beverage products, are disclosed containing encapsulated probiotic bacteria having resistance to subjection to at least thermal and acidic conditions. Beverage products include at least one aqueous liquid and capsules comprising a gelled mixture of alginate and denatured protein, and probiotic bacteria entrapped within the gelled mixture. The average particle size of the capsules is optionally less than 1000 microns (μm) in diameter, such as less than 500 μm in diameter. Methods are provided for making such encapsulated probiotics by providing a mixture comprising sodium alginate, denatured protein and active probiotic cells, and combining the mixture with a divalent cation to initiate cold gelation of the sodium alginate and denatured protein to form a second mixture. The second mixture is passed through an opening having a diameter of less than 1000 μm to form capsules. The weight ratio of protein to alginate is from 1:1 to 9:1.

17 Claims, 9 Drawing Sheets

(51) Int. Cl.
*A23P 10/30*          (2016.01)
*A23L 29/256*         (2016.01)
*A23L 27/30*          (2016.01)
*A23L 33/135*         (2016.01)
*A23L 33/155*         (2016.01)
*A23L 33/16*          (2016.01)
*A23L 33/19*          (2016.01)
*A23L 2/02*           (2006.01)
*A23L 2/60*           (2006.01)
*A23L 2/66*           (2006.01)
*A23L 2/68*           (2006.01)
*A61K 35/745*         (2015.01)
*A61K 35/747*         (2015.01)
*C12N 1/04*           (2006.01)
*C12N 11/04*          (2006.01)
*C12N 11/10*          (2006.01)
*B01J 13/04*          (2006.01)
*B01J 13/20*          (2006.01)

(52) U.S. Cl.
CPC ............... *A23L 2/68* (2013.01); *A23L 27/30* (2016.08); *A23L 29/256* (2016.08); *A23L 33/135* (2016.08); *A23L 33/155* (2016.08); *A23L 33/16* (2016.08); *A23L 33/19* (2016.08); *A23P 10/30* (2016.08); *A61K 35/745* (2013.01); *A61K 35/747* (2013.01); *B01J 13/046* (2013.01); *B01J 13/206* (2013.01); *C12N 1/04* (2013.01); *C12N 11/04* (2013.01); *C12N 11/10* (2013.01); *A23V 2002/00* (2013.01); *A23Y 2220/03* (2013.01); *A23Y 2300/00* (2013.01)

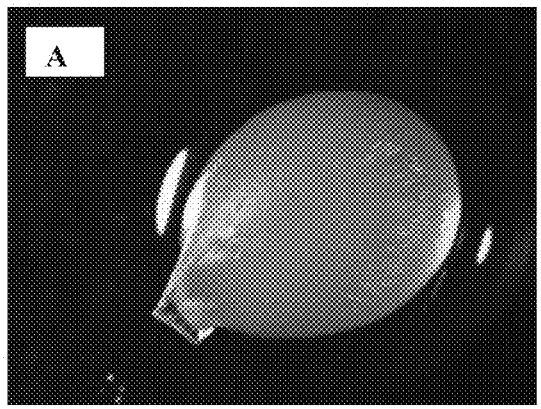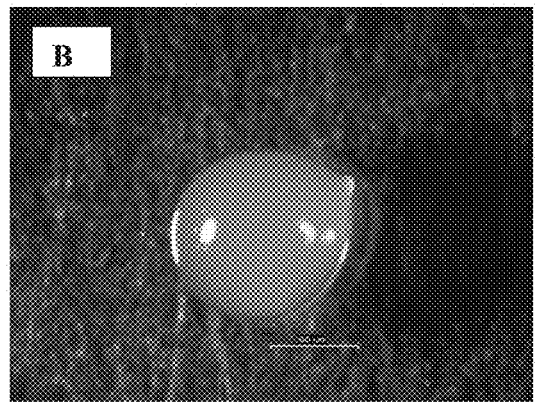
FIG. 1A        FIG. 1B
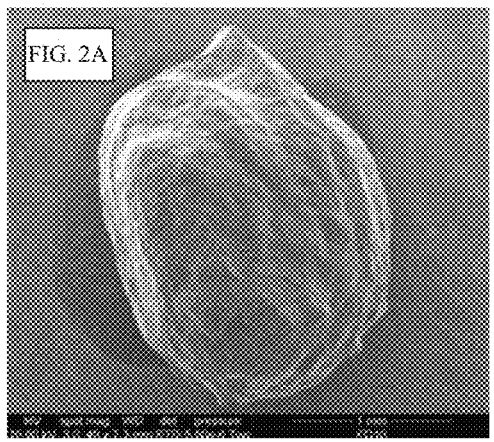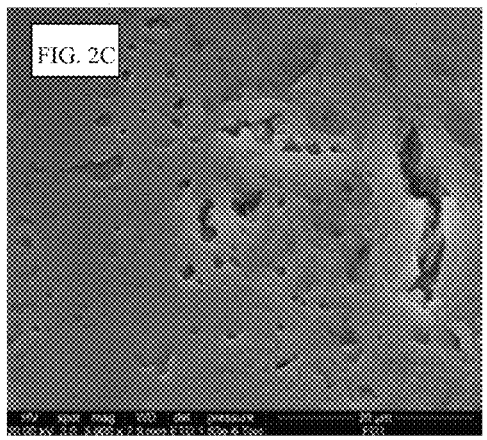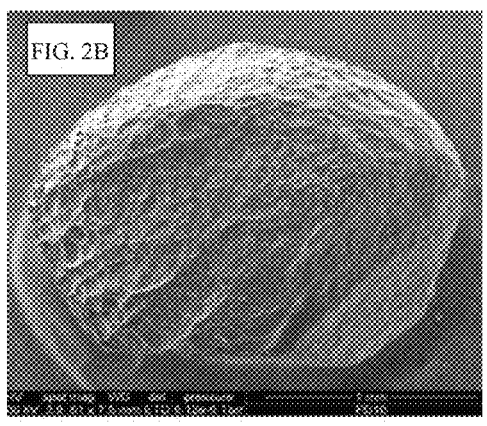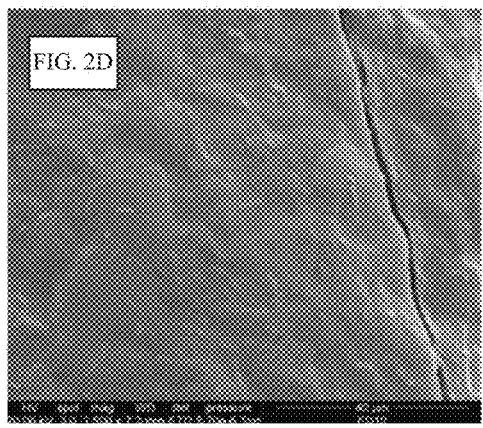

ENCAPSULATION SYSTEM FOR PROTECTION OF PROBIOTICS DURING PROCESSING

This application is a continuation of U.S. patent application Ser. No. 13/088,165, entitled "Encapsulation System for Protection of Probiotics During Processing," filed on Apr. 15, 2011, and published as US 2012/0263826-A1 on Oct. 18, 2012, the technical disclosure of which is hereby incorporated by reference in its entirety.

FIELD OF THE INVENTION

The present invention relates to the field of delivering particular ingredients to a consumer in comestibles, more particularly encapsulated nutrients such as probiotic bacteria in comestible products (e.g., juice beverages, beverage concentrates, ready to drink liquid formulations, syrups, powders, snacks, puddings, etc.).

BACKGROUND

Probiotic bacteria (referred to here in some cases as probiotics) are live bacterial microbes that beneficially influence the health and nutrition of individuals by promoting a healthier microflora in the host's intestine. These microflora are dependent on substances fed to them from the diet of the host organism. Probiotics typically colonize in the large intestine and can serve either or both of at least two major roles: they can supplement the natural flora of the gastrointestinal tract with additional bacteria, and they can be effective in treating a number of health conditions, including, but not limited to (1) alleviation of intestinal disorders (e.g., constipation and diarrhea caused by an infection by pathogenic organisms, antibiotics, chemotherapy, etc.); (2) stimulation and modulation of the immune system; (3) anti-tumoral effects resulting from inactivation or inhibition of carcinogenic compounds present in the gastrointestinal tract by reduction of intestinal bacterial enzymatic activities (e.g., O-glucuronidase, azoreductase, nitroreductase, etc.); (4) reduced production of toxic final products (e.g., ammonia, phenols, other protein metabolites known to influence hepatic cirrhosis, etc.); (5) reduction of serum cholesterol and arterial pressure; (6) maintenance of mucosal integrity; (7) alleviation of lactose intolerance symptoms; and/or (8) prevention of vaginitis.

Potential mechanisms of anti-pathogenic effects of probiotic bacteria are through decreasing the luminal pH by the production of short chain fatty acids such as acetic acid, lactic acid or propionic acid, rendering vital nutrients unavailable to pathogens, altering the redox potential of the environment, producing hydrogen peroxide or producing bacteriocins or other inhibitory substances (Kailasapathy and Chin, 2000). In recent years, the specific live microbial food ingredients and their effects on human health have been studied both within food matrices and as single or mixed culture preparations. Due to their perceived health benefits, probiotic bacteria have been increasingly included in fermented dairy products. Probiotics have been incorporated into fermented milks, yoghurts, soft, semi-hard and hard cheese, ice cream, and frozen fermented dairy desserts. Some of the most common types of probiotic bacteria include *Lactobacillus* and *Bifidobacteria* (Axelsson, 1993; Holzapfel et al., 2001).

The ability of probiotic microorganisms to survive and multiply in the host strongly influences their probiotic benefits. The bacteria should be metabolically stable and active in the product, survive passage through the upper digestive tract in large numbers and have beneficial effects when in the intestine of the host (Gilliland, 1989). The typical standard for any food sold with health claims from the addition of probiotics is that it contains at least $10^9$-$10^{10}$ colony forming units (CFU) of viable probiotic bacteria per serving. Probiotics are sensitive to various environmental conditions and typically lack the ability to survive for long periods of time in "high acid" foods and beverage products (e.g., fresh citrus fruits, citrus fruit juices, foods containing citrus fruit juices, tomato sauce, etc.). For example, in fruit juice beverage products probiotics are sensitive to numerous environmental conditions, including, e.g., low pH, high acid content, high water activity, heat, air, light, and the inherent presence of polyphenols found in fruit juices, or other environmental influences. Thus, the viability (measured in colony forming units or CFU), and therefore the efficacy, in comestibles supplemented with probiotics and in the gastrointestinal tract can be substantially reduced.

If an edible composition has a pH of less than 7 it is considered acidic. The acids present in an edible composition (e.g., a food or beverage product) contribute to the pH level. The more acid present, the lower the pH is likely to be. High-acid edible compositions are generally considered to have a natural pH of 4.6 or below. For example, one of the dominant nutrients in citrus fruit is acid, e.g., ascorbic acid (Vitamin C), and the pH level of orange juice is around 3.8. Acidic environments are known to denature vital proteins necessary for the growth of bacterial organisms. Consequently, the organisms die in an acidic environment. Many desirable probiotics grow best at pH values around 7.0. The terms "acid content" and "degree of acidity" can be distinguished. The acid content is a measure of how much acid is present per unit volume of the edible composition. The degree of acidity is the actual pH value of the food or beverage. A high acid content gives a lower pH value, whereas a low acid content results in a higher pH value.

Heat (e.g., in the form of pasteurization) is routinely used to kill microbes that may be present in foods. In general, the cooler a product can be maintained, the greater the probiotic survival. Sunlight or artificial light can also kill at least some probiotics. Certain wavelengths of UV light are especially harmful. Due to probiotic sensitivity, environmental influences like high temperatures, high oxygen levels, moisture and direct light may result in beverages containing these organisms having a short shelf life. The result is a product with an inadequate shelf life, that is, a product whose decreased probiotic cell count determines the end of the product's shelf life, leading to higher costs and increased waste.

Encapsulation techniques, such as microencapsulation, have been investigated for use to enhance processing, storage and digestive stability of sensitive materials, such as probiotic bacteria, allowing stabilization and temporal and targeted release of ingredients. Microencapsulation has been defined as a technology of packaging solids, liquids or gaseous materials in miniature, sealed capsules that can release their contents at controlled rates under the influences of specific conditions (Anal and Stevens, 2005; Anal at al., 2006). Microencapsulation has been used to enhance processing, storage and digestive stability of sensitive materials, such as probiotic bacteria. This technology allows materials to be coated or entrapped in a matrix creating a barrier to the surrounding environment, which is subsequently degraded to release the core material. The composition of microcapsules may be manipulated to improve stability and allow degradation under specific conditions (Anal and Singh, 2007). The goal of microencapsulation of probiotic bacteria is thus to prevent damage during processing and storage and from degradation by gastric acid, proteolytic enzymes and bile salts before targeted release in the colon.

To date, the research on encapsulation of probiotics has mainly focused on maintaining viability of probiotic bacterial cells at low pH and high bile concentrations, as well as during spray drying, freeze drying and storage. Much research has focused on microencapsulation technologies and the manipulation of encapsulation parameters, such as coating material types and their concentrations and the use of multiple coating layers. A few attempts have been made to improve the viability of probiotics at high temperatures by adding thermoprotectants, however the viability has been found to be negligible with many strains. Consequently, there appear to be no commercial probiotic products available that are stable at high temperatures. Moreover, prior encapsulation methods have required employment of water-in-oil or oil-in-water emulsions, multiple reaction steps, multiple encapsulation coatings or shells, or combinations thereof.

Consumers demonstrate continued interest in comestible products such as ready-to-drink (RTD) beverages or foods fortified with ingredients believed to provide health benefits. It would be desirable to provide probiotics or other nutrients in a stable form for use in comestible products, so that the ingredients can withstand certain process conditions related to processing (e.g., mixing, homogenizing, pasteurizing, etc.) of the comestible, yet would be available as a nutrient within the gastrointestinal tract, once the food or beverage is consumed by an individual.

Various documents including, for example, publications and patents, are recited throughout this disclosure. All such documents are hereby incorporated by reference. The citation of any given document is not to be construed as an admission that it is prior art with respect to the present invention. To the extent that any meaning or definition of a term in this written document conflicts with any meaning or definition of the term in a document incorporated by reference, the meaning or definition implied or assigned to the term in this written document shall govern.

SUMMARY OF THE INVENTION

The following presents a simplified summary of aspects of the inventive products, formulations and methods disclosed here. This summary is not an extensive overview, and it is not intended to identify all or only key or critical elements or to delineate the scope of the inventive products, formulations and methods covered by the claims. The following summary merely presents some concepts and aspects of the disclosure in a simplified form as a prelude to the more detailed description provided below of certain exemplary and non-limiting embodiments of the invention.

In a first aspect, the invention is directed to a beverage product comprising at least one aqueous liquid, and capsules comprising a gelled mixture of alginate and whey protein isolate, and probiotic bacteria entrapped within the gelled mixture. The capsules comprise an average particle size of between 1 micron and 1000 microns ($\mu$m) in diameter. The probiotic bacteria optionally comprise *Bifidobacterium* spp., *Lactobacillus* spp., or mixtures of any of them. The entrapped probiotic bacteria is thermally stabilized, wherein subjection of the beverage product to a temperature of up to 92 degrees Celsius for up to 5 seconds results in a decrease of viable probiotic bacteria cells of between 0 and $1 \times 10^3$ CFU per gram capsules.

In a second aspect, the invention is directed to a method of forming encapsulated probiotics comprising mixing an aqueous solution comprising sodium alginate and denatured protein with a suspension of active probiotic cells in 0.1% peptone water, to form a first mixture, combining the first mixture with an aqueous calcium chloride solution to initiate cold gelation of the sodium alginate and denatured protein to form a second mixture; and passing the second mixture through an opening having a diameter of less than 1000 $\mu$m to form beads having an average particle size of less than 1000 $\mu$m in diameter, wherein the resulting uncoated beads comprise a gelled mixture of alginate and denatured protein and probiotic bacteria entrapped within the gelled mixture. In certain embodiments the ratio of protein to alginate is from 1:1 to 9:1.

In a third aspect, the invention is directed to a food product comprising encapsulated probiotic bacteria. The encapsulated probiotic bacteria is provided by capsules comprising a gelled mixture of alginate and denatured whey protein isolate, and probiotic bacteria entrapped within the gelled mixture. The capsules comprise an average particle size of between 1 $\mu$m and 1000 $\mu$m in diameter.

In a fourth aspect, the invention is directed to a method of forming encapsulated probiotics consisting essentially of providing a mixture comprising sodium alginate, denatured protein and active probiotic cells, and combining the mixture with a divalent cation to initiate cold gelation of the sodium alginate and the denatured protein, wherein the resulting capsules comprise a gelled mixture of alginate and denatured protein, and probiotic bacteria entrapped within the gelled mixture. The weight ratio of protein to alginate is from 1:1 to 9:1.

In a fifth aspect, the invention is directed to a method of preparing uncoated gelled beads comprising mixing an aqueous solution comprising sodium alginate and denatured protein with a suspension of active probiotic cells in 0.1% peptone water, combining the first mixture with a divalent cation to initiate cold gelation of the sodium alginate and denatured protein to form a second mixture, and passing the second mixture through an opening having a diameter of less than 1000 $\mu$m to form beads having an average particles size of less than 1000 $\mu$m, wherein the resulting capsules comprise a gelled mixture of alginate and denatured protein, and probiotic bacteria entrapped within the gelled mixture. The weight ratio of protein to alginate is from 1:1 to 9:1.

In a sixth aspect, the invention is directed to capsules formed by the method of mixing an aqueous solution comprising sodium alginate and denatured protein with active probiotic cells to form a first mixture, combining the first mixture with an aqueous calcium chloride solution to initiate cold gelation of the sodium alginate and denatured protein to form a second mixture, and passing the second mixture through an opening to form capsules having an average particle size of between 1 $\mu$m and 1000 $\mu$m in diameter. The resulting capsules comprise a gelled mixture of alginate and denatured protein, and probiotic bacteria entrapped within the gelled mixture. Moreover, the method results in capsules in which the protein is not significantly covalently bonded to the alginate. The weight ratio of protein to alginate is from 1:1 to 9:1.

In certain exemplary embodiments, the food or beverage products additionally include one or more ingredients suitable for use in such comestible products, including, e.g., one or more of any of the additional ingredients disclosed below. All percentages recited in the description, disclosure and the appended claims are percent by weight of the fully formulated food or beverage product unless otherwise stated.

BRIEF DESCRIPTION OF THE DRAWINGS

A more complete understanding of the present disclosure and the advantages thereof may be acquired by referring to the following description in consideration of the accompanying drawings, in which like reference numbers indicate like features, and where FIG. 1A depicts a digital light microscopic image of a pure whey protein capsule.

FIG. 1B depicts a digital light microscopic image of a 75:25 whey protein isolate to alginate capsule FIG. 2A depicts a scanning electron microscopic image of a freeze-dried pure whey protein isolate capsule.

FIG. 2B depicts a scanning electron microscopic image of a freeze-dried 50:50 whey protein isolate to alginate capsule.

FIG. 2C depicts a scanning electron microscopic image of pores on the surface of a pure whey protein isolate capsule.

FIG. 2D depicts a scanning electron microscopic image of *L. acidophilus* cells on the surface of a thermally denatured whey protein isolate capsule.

DETAILED DESCRIPTION OF THE INVENTION

Figure 3:
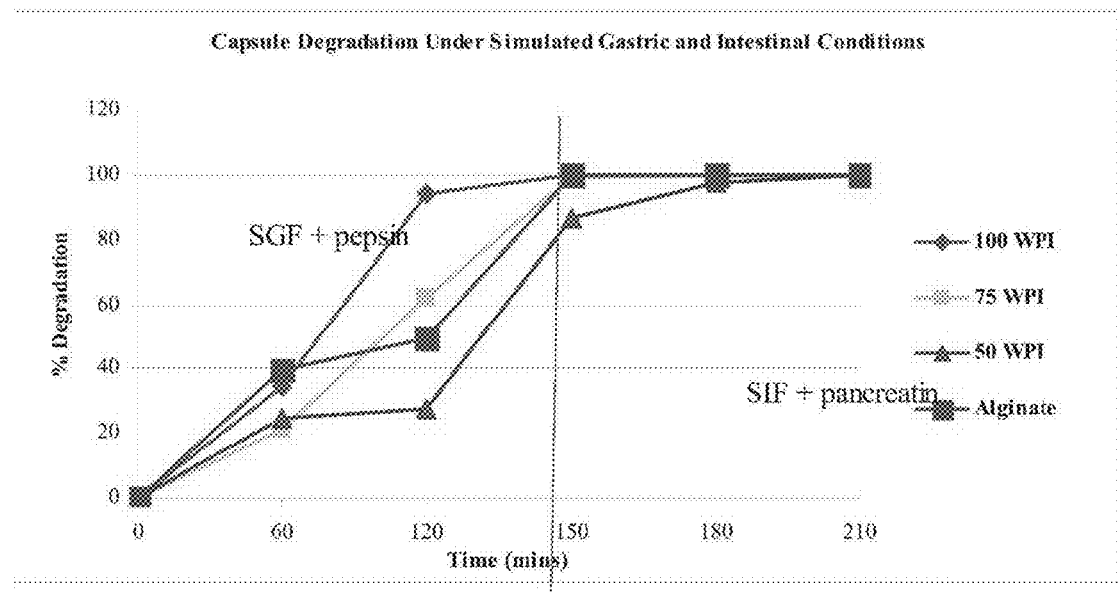
FIG. 3 depicts the degradation of capsules in simulated gastric fluid and simulated intestinal fluid.

In the following description of the various embodiments, reference is made to the accompanying figures, which form a part hereof, and in which is shown by way of illustration various embodiments in which one or more aspects of the disclosure may be practiced. For convenience, the various embodiments discussed below are formulations, products, methods and the like. It is to be understood that other embodiments may be utilized and structural and functional modifications may be made without departing from the scope of the present disclosure.

Referenced herein are trade names for components including various ingredients suitable for use in the exemplary beverage products, formulations and methods disclosed herein. The inventors do not intend to be limited by materials under a certain trade name. Equivalent materials (e.g., those obtained from a different source under a different name or reference number) to those referenced herein by trade name may be substituted and utilized in the descriptions herein.

Aspects of the invention are directed to the use of food grade biopolymers as suitable encapsulating agents for probiotic bacteria. Such aspects provide a food-grade biopolymer system which encapsulates and stabilizes probiotic bacteria in thermal and gastric conditions as well as enables delivery of the probiotic bacteria to the lower gastrointestinal tract. In certain aspects of the invention, *Lactobacillus* and *Bifidobacterium* cells are encapsulated in mixtures of thermally denatured whey protein isolate in combination with alginate. Various combinations of these biopolymers have been investigated to produce strong and highly desirable capsules. According to certain embodiments, capsules are prepared using an extrusion encapsulation method, having an ability to protect bacterial cells under thermal and gastrointestinal conditions. In addition, sensory tests of orange juice and grape juice fortified with encapsulated probiotic bacteria cells show no significant flavor impact provided by the encapsulated probiotic bacteria.

The shelf life of a beverage product containing probiotics may be defined as the time duration during which it retains at least a certain concentration or level of viable probiotics, e.g., at least $1.0 \times 10^8$ CFU/volume or mass unit, or in some cases at least $5.0 \times 10^9$ CFU/volume or mass unit. The volume or mass unit may be milliliters (mL), grams (g), ounces (oz.), etc. According to certain embodiments of the invention, comestible products are provided comprising encapsulated viable probiotic bacteria in an amount of at least $1.0 \times 10^9$ CFU per serving, such as an 8 ounce serving or a 240 mL serving.

The thermal stability of encapsulated probiotic bacteria may be defined as the time duration at a temperature above ambient at which they retain at least a certain concentration or level of viable probiotics, e.g., at least $1.0 \times 10^8$ CFU/volume or mass unit, or in some cases at least $5.0 \times 10^9$ CFU/volume or mass unit. According to certain embodiments of the invention, comestible products are provided comprising encapsulated viable probiotic bacteria in an amount of at least $1.0 \times 10^6$ CFU per serving. The temperature above ambient at which the encapsulated probiotic bacteria, such as a comestible product containing the encapsulated probiotic bacteria, may be subjected comprises 28 to 95 degrees Celsius, for example, 30 degrees Celsius, or 35 degrees Celsius, or 40 degrees Celsius, or 45 degrees Celsius, or 50 degrees Celsius, or 55 degrees Celsius, or 60 degrees Celsius, or 65 degrees Celsius, or 70 degrees Celsius, or 75 degrees Celsius, or 80 degrees Celsius, or 85 degrees Celsius, or 90 degrees Celsius, or 92 degrees Celsius, wherein any of these temperatures may reflect an end point in a range. The time duration of subjection to the temperature above ambient comprises 3 seconds to an hour, for example, 4 seconds, or 5 seconds, or 10 seconds, or 20 seconds, or 30 seconds, or 45 seconds, or 1 minute, or three minutes, or five minutes, or seven minutes, or ten minutes, or fifteen minutes, or twenty minutes, or twenty-five minutes, or thirty minutes, or forty-five minutes, or an hour, wherein any of these times may reflect an end point in a range. Typically, the higher the temperature, the shorter the time duration is at which the probiotic will be successfully thermally protected.

Certain exemplary and non-limiting embodiments of the comestible product or formulations disclosed herein can maintain high probiotic bacterial viability rates and so survive subjection to elevated temperatures, such as for example and without limitation, thermal processing during preparation of the comestible, destruction of undesirable microbes in the comestible, or combinations thereof. These exemplary beverage products or formulations, from a starting concentration ranging from $1.0 \times 10^9$-$1.0 \times 10^{12}$ CFU/gram capsules, e.g., $1.0 \times 10^{16}$ CFU/gram capsules, are capable of delivering at least $1.0 \times 10^6$ CFU/gram capsules following subjection to elevated temperatures. According to aspects of the invention, the decrease of viable probiotic bacteria upon subjection to elevated temperature comprises 0 to $1.0 \times 10^4$ CFU/gram capsules, or 0 to $5.0 \times 10^3$ CFU/gram capsules, or 0 to $1.0 \times 10^3$ CFU/gram capsules, or 0 to $5.0 \times 10^3$ CFU/gram capsules, or 0 to $1.0 \times 10^2$ CFU/gram capsules, or 0 to 50 CFU/gram capsules, or 0 to 10 CFU/gram capsules.

Certain exemplary and non-limiting embodiments of the comestible products or formulations disclosed herein can maintain high probiotic bacterial viability rates and so achieve a long shelf life. These exemplary beverage products or formulations, from a starting concentration ranging from $1.0 \times 10^9$-$1.0 \times 10^{12}$ CFU/serving, e.g., $1.0 \times 10^{10}$ CFU/12 serving, are capable of delivering at least $1.0 \times 10^9$ CFU bacteria per 12 fluid ounces of beverage, for example, when consumed even after 45 days when stored in the dark or in otherwise UV shielded conditions at a temperature of 35° F. post-filling. In certain exemplary and non-limiting embodiments, fully one-half of the starting concentration of viable probiotic bacteria remains after 45 days, or 63 days, or even 70 days, when stored in the dark or in otherwise UV shielded conditions at a temperature of 35° F. post-filling. According to exemplary aspects of the present invention the decrease in viable encapsulated probiotic bacteria in an acidic juice comprising pH 3.75 and stored in ambient conditions comprises 0 to $1.0 \times 10^3$ CFU/gram capsules after ten weeks storage at 35° F. post-filling, i.e., $1.0 \times 10^6$-$1.0 \times 10^{12}$ CFU/gram capsules.

Moreover, the pH of a comestible product according to aspects of the invention can affect the viability of probiotic bacteria, with lower pH values decreasing the viability of the probiotic bacteria. For instance, according to exemplary aspects of the present invention the decrease in viable encapsulated probiotic bacteria in an acidic juice comprising pH 2.75 and stored in ambient conditions comprises 0 to 100 CFU/gram capsules after two weeks storage. In contrast, the decrease in viable encapsulated probiotic bacteria in an acidic juice comprising pH 3.5 and stored in ambient conditions comprises 0 to 100 CFU/gram capsules after eight weeks storage.

As used herein and in the appended claims, the term "probiotics," "probiotic micro-organism," or "probiotic biomass" is understood to include any micro-organisms, cell content or metabolites from micro-organisms, having beneficial effects to its host. Therefore, yeasts, moulds and bacteria may be included. In certain exemplary embodiments, probiotic bacterial strains of *Bifidobacterium* may be used in the beverage products, formulations and methods disclosed here, including, e.g., *B. breve, B. animalis (lactis), B. longum, B. bifidum, B. adolescentis, B. thermophilum,* and *B. infantis.* Probiotic bacterial strains of the genus *Lactobacillus* may also be used, including, e.g., *L. acidophilus, L. casei, L. rhamnosus, L. paracasei, L. johnsonii, L. reuteri* and *L. plantarum, L. lactis, L. bulgaricus.*

EP 0862863 lists some examples for probiotics presently known. For example, strains of *Lactobacillus plantarum* (Lp299), *Bifidobacterium lactis* (HN019), or *Bifidobacterium lactis* (BB-12) may be used in certain non-limiting examples of the comestible products and formulations disclosed here. A selection of different probiotic strains is offered by Christian Hansen BioSystems A/S (CHL), 10-12 Boge All, P.O Box 407, DK-2970 Horsholm, Denmark. It will be within the ability of those skilled in the art, given the benefit of this disclosure, to select suitable additional or alternative strains of probiotic bacteria for use in various embodiments of the beverage products and formulations disclosed here.

In some exemplary and non-limiting embodiments, comestible products or formulations may contain bacteria from multiple species. In certain exemplary and non-limiting examples, when two bacteria are present in a formulation, the bacteria may be, for example, *B. animalis (lactis)* and *L. rhamnosus.* The ratio of one bacterial species to the other may vary widely. The ratio may be from about 0.00000001 to 1, about 0.0000001 to 1, about 0.000001 to 1, about 0.00001 to 1, about 0.0001 to 1, about 0.001 to 1, about 0.01 to 1, about 0.1 to 1, or about 1 to 1.

Viable bacterial numbers are often reported as CFU, or colony forming units. One colony is formed by a single viable bacterium when the bacteria are plated at a suitable dilution for single colony formation. This is a standard technique known to microbiologists. Typically, the amount is expressed as the number of CFU in a liquid measure e.g., milliliters (ml), fluid ounces (fl. oz), etc., or in a solid measure e.g., grams (g). U.S. regulation 21 CFR 101.9(b)(5)(viii) defines a fluid ounce as exactly 30 ml. Sufficient numbers of viable bacteria may be necessary to obtain the beneficial effects of the probiotic bacteria. Often bacteria are packaged at a certain level of viable bacteria; however, before consumption, the levels may decrease thereby preventing the consumer from acquiring a beneficial dose of bacteria. Indeed, the National Center for Complementary and Alternative Medicine (NCCAM) has identified several issues relating to the quality of probiotic products including: viability of the bacteria in the product, types and titer of bacteria in the product, and stability under storage. See NCCAM, "BACKGROUNDER: Biologically Based Practices: An Overview" (October, 2004). This document may be found at the website of the National Center for Complementary and Alternative Medicine (NCCAM).

The bacteria suitable for certain exemplary and non-limiting examples of the beverage products, formulations and methods disclosed here may be prepared in a variety of methods known in the art, including, for example, growth on media containing casein. Optionally, the bacteria may be grown without casein, providing a completely dairy-free bacterial preparation. In certain exemplary and non-limiting embodiments, the bacteria may be stored by refrigeration, freezing, or freeze-drying without diminishing viability below a desired level. According to an aspect, the bacteria are frozen and then thawed prior to encapsulation. In accordance with certain aspects, the bacteria are freeze-dried and then measured, mixed and rehydrated in 0.10% peptone water prior to encapsulation.

Viable probiotic bacteria cells are encapsulated according to embodiments of the invention, in food biopolymeric capsules, such as beads or microcapsules. As used herein, the term "capsule" refers to a substantially completely enclosed particle. The enclosed particle may comprise an outer shell material that is the same or different from the interior material. For example and without limitation, a capsule may comprise one or more outer solid shells surrounding a liquid interior, or one or more solid outer shells surrounding a solid interior. According to aspects of the invention, both the outer shell and the interior material comprise a network comprising at least two biopolymers that are interspersed, cross-linked, or combinations thereof. For instance, according to certain aspects of the invention a capsule is provided comprising an outer shell and an interior material comprising the same biopolymers, wherein the difference between the outer shell and interior material is the extent of cross-linking of at least one of the biopolymers such that dense polymerization at the surface of the capsule forms an outer shell. In contrast, the extent of polymerization of the interior material is such that it comprises space between individual polymeric strands. When the capsule is composed of material present in a form that is a solid in both the interior and the outer shell of the capsule, it may be referred to herein as a "bead".

The size of the capsules (or beads) according to the invention varies depending on the process employed to prepare the capsules, and ranges between comprising an average particle size of between 1 μm and 3000 μm in diameter. Typically, combining a divalent cation source with the alginate using a dropwise method results in capsules at the higher end of the range, such as between 1500 μm in diameter and 3000 μm in diameter. The average particle size of the capsules may be controlled using methods and apparatuses known to those of skill in the art, such as for example and without limitation, spraying or extruding. For instance, once gelation of the capsule has begun, the mixture may be passed through openings in an extrusion apparatus, such as one or more nozzles, thereby resulting in the formation of capsules or beads comprising approximately the same diameter as the diameter of the opening through which the mixture was passed.

As used herein, the term "microcapsule" refers to a capsule (or bead) comprising an average particle size of between 1 μm and 1000 μm in diameter, such as between 1 μm and 900 μm in diameter, or between 1 μm and 800 μm in diameter, or between 1 μm and 700 μm in diameter, or between 1 μm and 600 μm in diameter, or between 1 μm and 500 μm in diameter, or between 1 μm and 400 μm in diameter, or between 1 μm and 300 μm in diameter, or between 1 μm and 200 μm in diameter, or between 1 μm and 100 μm in diameter, or between 100 μm and 600 μm in diameter, or between 200 μm and 600 μm in diameter, or between 400 μm and 600 μm in diameter, or between 300 μm and 500 μm in diameter. Capsules, including beads and microcapsules, comprise any shape formed during gelation of the biopolymers, for example and without limitation spherical, ovoid, cylindrical, and the like.

According to embodiments of the invention, biopolymers employed include for example and without limitation, proteins, polysaccharides and combinations thereof. Any suitable polysaccharide may be employed as is known in the art, such as for example and without limitation pectin, carrageenan, alginate, xanthan gum, modified celluloses, e.g., carboxymethylcellulose, gum acacia, gum ghatti, gum karaya, gum tragacanth, locust bean gum, guar gum, psyllium seed gum, quince seed gum, larch gum (arabinogalactans), stractan gum, agar, furcellaran, modified starches, gellan gum, fucoidan, and the like.

Any suitable protein source can be used as is known in the art, including for example, whey protein isolate, casein protein isolate, milk protein isolate, protein peptides, protein hydrolysates, rice protein, wheat protein, vegetable proteins, soy protein, soy protein peptides, soy protein hydrolysates, egg protein, legume proteins, proteins from tree nuts, proteins from ground nuts, corn zein protein, and the like. According to certain embodiments of the invention, the protein is denatured to improve the ability of the protein to substantially homogeneously mix or blend with the polysaccharide by reducing the three-dimensional size of the individual proteins. Denaturation may be performed by any suitable method known to those of skill in the art, for example and without limitation, by thermal methods. For instance, subjection of an aqueous solution of whey protein isolate to temperatures of between about 65 degrees Celsius and about 95 degrees Celsius for a time of 5 to 40 minutes will partially or completely denature whey protein isolate.

In an embodiment of the invention, two or more biopolymers are employed to form capsules for encapsulation of viable probiotic bacteria cells. The biopolymers alginate and protein, for instance sodium alginate and whey protein isolate, are successfully combined to form capsules containing probiotic bacteria. Alginate is an anionic polysaccharide that is commonly available as a sodium or potassium salt (i.e., sodium alginate or potassium alginate). When alginate is exposed to divalent cations such as $Ca^{2+}$, the alginate undergoes gelation to form a gel capsule (or a bead). Moreover, the process of denaturing protein exposes reactive groups and the denatured protein also undergoes gelation upon exposure to divalent cations. Consequently, a mixture of two or more biopolymers, for instance alginate and denatured protein, which is exposed to divalent cations, may form a plurality of capsules comprising a gelled mixture of alginate and denatured protein. Probiotic bacteria present in the mixture of the biopolymers become entrapped within the gelled mixture. Any suitable divalent cation known to those of skill in the art may be employed, in particular divalent cations approved for inclusion in comestibles, such as $Ca^{2+}$, $Mg^{2+}$, or $Fe^{2+}$, for example.

As the alginate and denatured protein undergo gelation, there is some intertwining of the alginate and protein; however, the denatured protein does not significantly chemically react with the alginate to form covalent bonds with the alginate polymer. As used herein, "substantially chemically unreacted" is defined as being from 90% to 100% unreacted. At low pH values, however, alginate and denatured protein in solution may form complexes of alginate and protein over time.

It is possible to incorporate additional materials into the capsule by providing a solution or dispersion of the alginate, protein, and the one or more other materials, prior to exposure to the divalent cations. Upon gelation, the one or more other materials become fixed (i.e., entrapped) within the capsule as an interior filling, as part of the gelled structure, or combinations thereof. According to aspects of the invention, one or more types of probiotic bacteria cells are included in an aqueous solution with the alginate and the denatured protein prior to gelation.

Surprisingly, gelled capsules comprising a mixture of polysaccharide and protein provide successful protection of viable probiotic bacteria upon exposure to processing conditions, such as for example elevated temperature and pressure, and exposure to acidic conditions, such as simulated gastric fluid, yet also release the probiotic bacteria upon exposure to basic conditions, such as simulated intestinal fluid. It has been discovered that capsules comprising a weight ratio of protein to polysaccharide from 1:1 to 4:1 provide such protection to probiotic bacteria. In contrast to such combinations, capsules comprising either 100% protein or 100% polysaccharide were not capable of protecting probiotic bacteria from elevated temperature or acid conditions. According to aspects of the invention, the weight ratio of protein (e.g., denatured whey protein isolate) to polysaccharide (e.g., sodium alginate) is from 1:1 to 4:1, or 1:1 to 9:1, or 1:1 to 8:1, or 1:1 to 7:1, or 1:1 to 6:1, or 1:1 to 5:1, or 2:1 to 3:1, or 5:1, or 4.5:1, or 4:1, or 3.5:1, or 3:1, or 2.5:1, or 2:1, or 1.5:1, or 1:1.

In certain embodiments of the invention, a method of preparing encapsulated probiotic bacteria is provided, comprising mixing an aqueous solution of sodium alginate with an aqueous solution of denatured protein and a suspension of active probiotic cells in 0.1% peptone water, to form a first mixture. As used herein, the term "peptone" refers to one or more water-soluble protein derivatives, which are obtained via partial hydrolysis of a protein by an acid or enzyme. Peptone is typically employed in culture media in bacteriology and known to those of ordinary skill in the art. As used herein, the term "0.1% peptone water" refers to an aqueous solution comprising 0.1% by weight peptone. Optionally, the first mixture is incubated in a water bath at a temperature between 36 and 46 degrees Celsius for at least 5 minutes, for example from 5 to 20 minutes. In alternate variations of embodiments, a method of preparing encapsulated probiotic bacteria comprises providing a first aqueous solution comprising sodium alginate (or another biopolymer), denatured protein, and active probiotic cells. The method comprises combining the first mixture (or first aqueous solution) with an aqueous solution comprising one or more divalent cations to initiate cold gelation of the sodium alginate and denatured protein to form a second mixture, and passing the second mixture through an opening, for instance an opening having a diameter of less than 1000 µm, to form capsules having an average particle size of between 1 µm and 1000 µm in diameter. The divalent cation comprises any suitable divalent cation, for example calcium chloride, which may be present at any suitable concentration of calcium chloride, such as about 4% weight per volume calcium chloride.

The resulting capsules comprise a gelled mixture of alginate and denatured protein, and comprise probiotic bacteria entrapped within the gelled mixture. According to aspects of the invention, the method further comprises hardening the capsules in a calcium chloride solution for at least fifteen minutes, followed by washing the hardened capsules with water. In alternate embodiments, the capsules are not subjected to hardening, but are washed with water following manufacture.

According to certain embodiments of the invention, capsules comprising probiotic bacteria may be prepared employing a single aqueous reaction of biopolymer gelation, by which the mixture of alginate and protein is gelled upon contact with divalent cations. This is in contrast to more complicated encapsulation techniques in which emulsions are prepared (e.g., oil-in-water or water-in-oil emulsions), the outer surface of the capsules is subjected to chemical reaction, one or more protective coatings or shells are applied to the outer surface of the capsules, or combinations thereof. The capsules of the present invention provide protection from environmental conditions as discussed above, without the need for modification of the outer surface by chemical reaction or the addition of coatings or shells on the capsules.

Extrusion is optionally employed during formation of the capsules, in which the opening that the second mixture is passed through comprises a nozzle. During extrusion methods, the mixture is forced through an extrusion nozzle using pressure during the gelation process. One exemplary extrusion apparatus is discussed in the examples below, and it is within the skill of the art to select a suitable extrusion apparatus. According to exemplary aspects, the capsules made by the method comprise an average particle size of between 1 µm and 500 µm in diameter or between 1 µm and 300 µm in diameter, such as 250 µm in diameter. Typically, capsules having a diameter of 500 µm or less are made using extrusion of the second mixture.

In addition, it is contemplated that encapsulated probiotic bacteria according to aspects of the present invention will not affect desired physical properties of the comestible product. For example, it is contemplated that the capsules will not affect acceptable mouthfeel, or physical and chemical interactions with the mouth, or affect the taste of the finished product. According to aspects of the invention, the average particle size of the capsules should be small enough not to increase the viscosity of the comestible or to provide a noticeable change in the taste of the comestible.

In certain embodiments, the denatured protein comprises denatured whey protein isolate. The capsules optionally comprise a weight ratio of denatured protein to alginate in a range of from 1:1 to 9:1, or in a range of from 1:1 to 4:1, or in a range of from 2:1 to 3:1. According to aspects of the invention, the capsules comprise at least $1 \times 10^9$ CFU/gram capsules of probiotic bacteria at the time of manufacture, such as at least $1 \times 10^{10}$ CFU/gram capsules of probiotic bacteria at the time of manufacture.

In embodiments of the invention, capsules comprising active probiotic bacteria are added to a comestible product and the comestible product is packaged, for eventual consumption by an individual. The amount of capsules incorporated into a comestible product varies depending on the loading of viable probiotics in the capsules. In aspects of the invention, the comestible product comprises between 0.05 grams and 10.0 grams of capsules per unit measure of product (e.g., fluid ounce or gram of product), or between 0.1 grams and 8 grams of capsules per unit measure of product, or between 0.1 grams and 5 grams of capsules per unit measure of product, or between 0.1 grams and 3 grams of capsules per unit product, or between 0.1 and 1 gram of capsules per unit product. As discussed above, a typical amount of viable probiotic bacteria in a comestible comprises at least $1 \times 10^{10}$ CFU per serving of product. It will be within the abilities of one skill in the art after benefit of the present disclosure, to determine an appropriate amount of capsules to include in a specific product to provide at least $1 \times 10^9$ CFU per serving of product.

A particular amount of capsules is added, for example, to a beverage product (e.g., a ready-to-drink beverage, a powdered beverage, a beverage concentrate, etc.), a pudding, a snack, or another suitable comestible known in the art. According to an aspect, a beverage product comprises at least one aqueous liquid and capsules comprising gelled alginate and having denatured whey protein isolate and probiotic bacteria entrapped within the gelled mixture of alginate and denatured protein. Optionally, the capsules comprise an average particle size of between 1 micron (μm) and 1000 microns in diameter. The aqueous liquid comprises any suitable liquid for beverage products known to those of skill in the art, for example and without limitation water, carbonated water, fruit juice, vegetable juice, hydration drinks, smoothies, teas, coffees, dairy products such as milk, and combinations thereof. For instance, the beverage product optionally comprises a juice beverage.

The term "shelf life" as used herein refers to the length of time after a comestible product is packaged that it meets the applicable criteria for sale and consumption, including having at least a requisite minimum concentration of the probiotics. In certain exemplary and non-limiting embodiments, the shelf life is the time duration that a product meets such criteria and is otherwise suitable for consumption, when packaged in hermetically sealed 12 fluid ounce PET vessels and stored in the dark or in otherwise UV shielded conditions at a temperature of about 35° F., including continuing to have viable probiotics at a level of at least $1.0 \times 10^9$ CFU/12 fluid ounces of the comestible. It should be understood that the comestible products and formulations disclosed here can be stored and packaged in any suitable containers, including, e.g., containers of any desired size made of any suitable material(s). The forgoing definition of shelf life is given here for convenient reference and convenient explanation of the improved shelf life provided by some or all embodiments of the products and formulations disclosed herein. Those persons having ordinary skill in the art will understand from this disclosure, that corresponding or comparable improved shelf life will be achieved in some or all embodiments also under other storage or shelf life conditions, e.g., at other temperatures, in containers of other suitable materials and sizes, etc. while still accomplishing similar results.

In certain exemplary and non-limiting embodiments, the comestible products or formulations disclosed herein exhibit the characteristic that after 45 days of storage in the dark or in otherwise UV shielded conditions at refrigeration temperatures (e.g., 35° F.) after preparation of the beverage, the number of bacteria contained in the beverage has a value anywhere from about $1.0 \times 10^9$ CFU/12 fluid ounces to about $5.0 \times 10^{10}$ CFU/12 fluid ounces of beverage of beverage.

It should be understood that the term "about" is used here and in similar applications in this disclosure and the appended claims to account for ordinary inaccuracy and variability in measurement and the like.

In certain exemplary and non-limiting embodiments, beverage products or formulations disclosed here exhibit the characteristic that after 45 days of storage in the dark or in otherwise UV shielded conditions in refrigeration temperatures (e.g., 35° F.) after preparation of the product, the number of bacteria contained in a beverage product, for example, is from about $1.0 \times 10^9$ CFU/12 fluid ounces to about $5.0 \times 10^{10}$ CFU/12 fluid ounces of beverage product, and in some embodiments from about $2.0 \times 10^9$ CFU/12 fluid ounces of beverage product to about $5.0 \times 10^{10}$ CFU/12 fluid ounces of beverage product, and in some embodiments from about $3.0 \times 10^9$ CFU/12 fluid ounces of beverage product to about $5.0 \times 10^{10}$ CFU/12 fluid ounces of beverage product, and in some embodiments from about $4.0 \times 10^9$ CFU/12 fluid ounces of beverage product to about $5.0 \times 10^{10}$ CFU/12 fluid ounces of beverage product.

In certain exemplary and non-limiting embodiments, a beverage product formulation is provided which comprises at least one fruit juice and capsules comprising probiotic bacteria at a concentration of at least $1.0 \times 10^9$ CFU/12 fluid ounces, e.g., from $1.0 \times 10^9$ to $1.0 \times 10^{12}$ CFU/12 fluid ounces, where the beverage product formulation has a pH of at most 4.5 and an acid level between 0.5% and 1.0%. In certain exemplary and non-limiting embodiments, such beverage product formulations have at least a 10% greater probiotic concentration, e.g., a probiotic concentration that is at least 20% greater, at least 25% greater, at least 50% greater, at least 75% greater or even at least 90% greater than it would be for the same formulation comprising free probiotic bacteria cells, when tested after 45 days in hermetically sealed 12 fluid ounce PET vessels stored in the dark or in otherwise UV shielded conditions at 35° F. In certain exemplary and non-limiting embodiments, such beverage product formulations have at least a 10% greater probiotic concentration, e.g., a probiotic concentration that is at least 20% greater, at least 25% greater, at least 50% greater, at least 75% greater, or even at least 90% greater than it would be for the same formulation free probiotic bacteria cells, when tested after 63 days in hermetically sealed 12 fluid ounce PET vessels stored in the dark or in otherwise UV shielded conditions at 35° F. In certain exemplary and non-limiting embodiments, such beverage product formulations have at least a 10% greater probiotic concentration, e.g., a probiotic concentration that is at least 20% greater, at least 25% greater, at least 50% greater, at least 75% greater, or even at least 90% greater than it would be for the same formulation free probiotic bacteria cells, when tested after 70 days in hermetically sealed 12 fluid ounce PET vessels stored in the dark or in otherwise UV shielded conditions at 35° F.

In at least one exemplary method for preparing the beverage product or formulation disclosed here, the method comprises mixing together a number of ingredients to form a first mixture, all or some of which are optionally precombined in any order. The ingredients include at least one liquid and capsules comprising probiotic bacteria. In certain exemplary embodiments, the beverage products additionally include one or more beverage ingredients suitable for use in such beverage products, including, e.g., one or more of any of the additional beverage ingredients disclosed below. The first mixture is optionally heated to pasteurize the mixture before the addition of the capsules comprising probiotic bacteria. The capsules may be introduced to the first mixture either after, e.g., just after, the pasteurization step or after, e.g., just after, packaging of the beverage. The beverage product can be packaged into bottles, cartons, or vessels, e.g., into sterilized single or multi-serving size containers. Typical such containers are about 4 fluid ounces to 16 fluid ounces in size, e.g., 6 fluid ounces, 8 fluid ounces or 12 fluid ounces. The containers can be sealed by suitable methods known in the art. The sealed containers can be shipped or stored at ambient temperatures or optionally, under refrigeration. Refrigeration temperatures typically have a range from about 32° F. to 50° F. (0° C. to 10° C.). Often, the refrigeration temperature is about 35° F. to 43° F. (2° C. to 6° C.).

Fruit juice(s) employed in aspects of the invention may be in any one or more of various forms including, e.g., liquids, concentrates, extracts, purees, pastes, pulps, and the like. A suitable fruit juice for the beverage includes, e.g., orange juice. Suitable fruit juice combinations for the beverage products and formulations disclosed here include, e.g., a mixture of any one or more of the juice from grape, cranberry, apple, orange, mango, pineapple, and coconut. Bacterial species that exhibit excellent survival in beverage products comprising these mixtures include, e.g., *Bifidobacterium* spp., *Lactobacillus* spp. or mixtures of any of them.

Mixing should be accomplished such that the capsules are not destroyed. The mixer(s) can be selected for a specific application based, at least in part, on the type and amount of ingredients used, amount of ingredients used, the amount of product to be produced and the flow rate. Generally, a commercially available mixer, such as those available from Invensys APV of Getzville, N.Y. or Silverson Machines, Inc. of East Longmeadow, Mass., may be used.

The beverage product or formulation may be homogenized and/or pasteurized. Beverages may, in addition be further or post processed following the adding of the encapsulated probiotic bacteria. Post processing can include, for example, cooling the product solution and filling it into container for packaging and shipping. Post processing may also include deaeration of the food product to <4.0 ppm oxygen, preferably <2.0 ppm and more preferably <1.0 ppm oxygen. Deaeration, however, and other post processing tasks may be carried out prior to processing, prior to pasteurization, prior to mixing with the capsules and/or at the same time as adding the capsules. In addition, an inert gas (e.g., nitrogen) headspace may be maintained during the intermediary processing of the product and final packaging. Additionally/alternatively, an oxygen barrier and/or oxygen scavengers could be used in the final packaging.

In certain exemplary and non-limiting embodiments, the beverage product or formulation comprises not-from-concentrate (NFC) and/or from-concentrate (FC) juice(s). Juices suitable for use in some or all of the beverage products and formulations disclosed here include, e.g., juices from fruit or vegetable sources. Certain exemplary and non-limiting examples of such beverage products or formulations comprise one or more citrus juices, e.g., a not-from-concentrate (NFC) orange juice. Other types of fruit or vegetable juices include but are not limited to juices of citrus fruit (e.g., orange, grapefruit, lemon, lime, tangerine, tangelo), apricot, apple, kumquat, mango, pear, peach, pineapple, papaya, passion fruit, grape, strawberry, raspberry, cranberry, currant, bean, blueberry, blackberry, acai, lychee, kiwi, pomegranate, watermelon, aronia, tomato, celery, cucurbits, onion, watercress, cucumber, carrot, parsley, beet, rhubarb, asparagus, potato, turnip, rutabaga, and a combination of any of them. In certain exemplary and non-limiting embodiments, the beverage product or formulation comprises fruit juice (e.g., orange juice and/or other citrus juice) in an amount from about 5% to about 100% by weight of the beverage product, e.g., about 10% to about 100% by weight, about 10% to about 90% by weight, about 10% to about 75% by weight, about 15% to about 50% by weight, or about 20% to about 30% by weight.

In certain exemplary embodiments, the beverage product or formulation may include a vegetable component, including, but not limited to, one or more vegetable juices, extracts, powders, skins, rinds, grinds, roots, pulps, homogenized pulps, purees, or any combination thereof. The vegetable component can be used in the beverage product or formulation in any suitable amount or concentration effective to achieve the level of taste desired. When included in the mixture, the ratio of fruit juice to vegetable juice may vary, depending on the manner in which the vegetable and fruit juices are mixed and/or the beverage product to be produced. The ratio of fruit to vegetable juice will vary to suit a particular application and can include, for example, from 0:100 to 100:0, for example, 2:1, 3:1, or 3:2. In certain exemplary embodiments, the mixture of fruit juice and vegetable juice comprises about 80%-60% fruit juice and about 20%-40% vegetable juice. In certain exemplary embodiments, the fruit to vegetable juice ratio is about 80:20; however, other ratios are contemplated and within the scope of this disclosure.

Exemplary beverage products include, but are not limited to, any ingredient or any combination of ingredients, or any substance or any combinations of substances, that can be used or prepared for use as a beverage for a mammal and includes, but is not limited to, ready to drink liquid formulations, beverage concentrates, syrups, powders and the like. Exemplary beverage products include, but are not limited to, carbonated and non-carbonated beverages, fountain beverages, frozen ready-to-drink beverages, frozen carbonated beverages, beverage concentrates, powdered concentrates, coffee beverages, tea beverages, dairy beverages, flavored waters, enhanced waters, fruit juices, smoothies, fruit juice-flavored drinks, fruit-flavored drinks, sports drinks, soy drinks, hydration drinks, energy drinks, fortified/enhanced water drinks, vegetable drinks, grain-based drinks, malt beverages, fermented drinks, yogurt drinks, kefir, alcoholic beverages, and mixtures of any of them. Beverage products further include, e.g., full calorie drinks/beverages and reduced-calorie (e.g., light, diet, zero calorie) drinks/beverages. Beverage products include bottle, can, and carton products and fountain syrup applications.

In certain exemplary and non-limiting embodiments of the beverage products and formulations disclosed here, PET (polyethylene terephthalate) bottles capable of containing 12 fluid ounces are used as containers for the beverage. Methods of beverage preservation suitable for at least certain exemplary embodiments of the beverage products disclosed here include, e.g., aseptic packaging and/or heat treatment or thermal processing steps, e.g., tunnel pasteurization, hot filling, cold filling, refrigeration, etc. Such steps can be used to reduce yeast, mold and microbial growth in the beverage products. For example, U.S. Pat. No. 4,830,862 to Braun et al. discloses the use of pasteurization in the production of fruit juice beverages as well as the use of suitable preservatives in carbonated beverages. In general, heat treatment includes hot fill methods typically using high temperatures for a short time, e.g., about 190° F. (87.8° C.) for 10 seconds or about 92° C. for 4 seconds, tunnel pasteurization methods typically using lower temperatures for a longer time, e.g., about 160° F. (71.1° C.) for 10-15 minutes, and retort methods typically using, e.g., about 250° F. (121° C.) for 3-5 minutes at elevated pressure, i.e., at pressure above 1 atmosphere. Many cold filled products must also be refrigerated to ensure adequate shelf life. Cold fill temperatures are those that fall below the hot fill range, with some techniques requiring temperatures just above room temperature, some at 45° F., and some at 150°-160° F. Cold filling has traditionally been used for milk and various other dairy items, sparkling waters and wines, beers, and juices. Juice makers typically combine cold filling and pasteurization combinations in combination with refrigerated distribution and storage. Cold filled juices sold in a refrigerated state are typically packaged in plastic bottles or gabletop cartons.

In certain exemplary and non-limiting embodiments disclosed here, beverage products include, e.g., ready to drink liquid formulations, beverage concentrates and the like. At least certain exemplary embodiments of the beverage products contemplated are prepared with an initial volume of juice or juice concentrate to which additional ingredients are added. Full strength beverage products can be formed from the beverage concentrate by adding further volumes of water and/or other solvents to the concentrate. In certain exemplary and non-limiting embodiments of the beverage products and formulations disclosed here, the solvent may include e.g., water, ethanol, glycerin, propylene glycol, benzyl alcohol, isopropanol, triacetin, or mixtures of any of them. In certain other embodiments, a full strength beverage product is directly prepared without the formation of a concentrate and subsequent dilution.

The terms "beverage concentrate," and "syrup" are used interchangeably throughout this disclosure. At least certain exemplary embodiments of the beverage products contemplated are prepared with an initial volume of water to which additional beverage ingredients are added. Full strength beverage products can be formed from the beverage concentrate by adding further volumes of water to the concentrate (also known as diluting). Typically, for example, full strength beverage products can be prepared from the concentrates by combining approximately 1 part concentrate with between approximately 3 to approximately 7 parts water. In certain exemplary embodiments the full strength beverage product is prepared by combining 1 part concentrate with 5 parts water. In certain other embodiments, a full strength beverage is directly prepared without the formation of a concentrate and subsequent dilution.

In certain exemplary and non-limiting embodiments, the beverage product comprises juice with added water. Purified water can be used in the manufacture of certain exemplary embodiments of the beverage products or formulations disclosed here, and water of a standard beverage quality can be employed in order not to adversely affect beverage product or formulation taste, odor, or appearance. The water typically will be clear, colorless, free from objectionable minerals, tastes and odors, free from organic matter, low in alkalinity and of acceptable microbiological quality based on industry and government standards applicable at the time of producing the beverage product or formulation. In certain exemplary and non-limiting embodiments, water is added at a level of from about 0% to about 90% by weight of the beverage product, e.g., about 15% to about 80% by weight, about 40% to about 70% by weight, or about 50% to about 60% by weight. In certain exemplary embodiments the water used in beverages and concentrates disclosed here is "treated water," which refers to water that has been treated to remove substantially all mineral content of the water prior to optional supplementation with any of the components described here as disclosed in U.S. Pat. No. 7,052,725. Methods of producing treated water are known to those of ordinary skill in the art and include deionization, distillation, filtration and reverse osmosis ("R—O"), among others. The terms "treated water," "purified water," "demineralized water," "distilled water," and "R—O water" are understood to be generally synonymous in this discussion, referring to water from which substantially all mineral content has been removed, typically containing no more than about 500 ppm total dissolved solids, e.g., no more than about 250 ppm.

Various sweeteners may be included in the formulations of the beverage products or formulations disclosed here. The sweeteners are edible consumables suitable for consumption and for use in beverage products. By "edible consumables" is meant a food or beverage or an ingredient of a food or beverage for human or animal consumption. Suitable sweeteners or sweetening agents used in certain exemplary embodiments disclosed here include a non-nutritive and natural beverage ingredient or additive (or mixtures of any of them) which provides sweetness to the beverage, i.e., which is perceived as sweet by the sense of taste. The perception of flavoring agents and sweetening agents may depend to some extent on the interrelation of elements. Flavor and sweetness may also be perceived separately, i.e., flavor and sweetness perception may be both dependent upon each other and independent of each other. For example, when a large amount of a flavoring agent is used, a small amount of a sweetening agent may be readily perceptible and vice versa. Thus, the oral and olfactory interaction between a flavoring agent and a sweetening agent may involve the interrelationship of elements.

Sweeteners suitable for use in various exemplary and non-limiting embodiments of the beverage products and formulations disclosed here include natural sweeteners. Suitable sweeteners and combinations of sweeteners are selected for the desired nutritional characteristics, taste profile, beverage product or formulation mouthfeel and other organoleptic factors. Natural sweeteners suitable for at least certain exemplary embodiments include, but are not limited to, erythritol, tagatose, sorbitol, mannitol, xylitol, maltose, rhamnose, trehalose, glycyrrhizin, malitol, lactose, Lo Han Guo ("LHG"), a rebaudioside, a steviol glycoside, *Stevia rebaudiana* extract, xylose, arabinose, isomalt, lactitol, maltitol, and ribose, protein sweeteners (e.g., thaumatin, monellin, brazzein, monatin, etc.), and the like or combinations thereof. Natural non-nutritive sweeteners suitable for some or all embodiments of the beverage products or formulations disclosed here include, but are not limited to, a rebaudioside (e.g., a rebaudioside juice concentrate or rebaudioside powder having a rebaudioside content of from about 0.005% to about 99%, e.g., from about 0.005% to about 1.0%), other steviol glycosides (e.g., a steviol glycoside juice concentrate or steviol glycoside powder having a stevioside content of from about 0.005% to about 99%, e.g., from about 0.005% to about 1.0%), *Stevia rebaudiana* extract, Lo Han Guo (e.g., LHG juice concentrate or LHG powder having a mogroside V content of from about 0.005% to about 99%), monatin, glycyrrhizin, thaumatin, monellin, brazzein, and the like or mixtures of any two or more of them. Also, in certain exemplary and non-limiting embodiments of the beverage products and formulations disclosed here, combinations of one or more natural sweeteners are used to provide the sweetness and other aspects of desired taste profile and nutritive characteristics. It should also be recognized that certain such sweeteners will, either in addition or instead, act as tastants, masking agents or the like in various embodiments of the beverage products and formulations disclosed here, e.g., when used in amounts below its (or their) sweetness perception threshold in the beverage product or formulation in question.

Certain exemplary and non-limiting embodiments of the beverage products and formulations disclosed here include natural non-nutritive sweeteners, including, but not limited to, rebaudioside A, rebaudioside B, rebaudioside C, rebaudioside D, rebaudioside E, steviolbioside, stevioside, dulcoside A, other steviol glycosides, *Stevia rebaudiana* extract, Lo Han Guo (e.g., LHG juice concentrate, LHG powder, or mogroside V), thaumatin, monellin, brazzein, monatin, and the like or mixtures of any two or more of them. LHG, if used, may have, for example, mogroside V content of from about 0.005% to about 99%. Optionally, the sweetener or sweetener component may include erythritol, tagatose, or a mixture of the two. Non-nutritive, high potency sweeteners typically are used at a level of milligrams per fluid ounce of beverage product, depending on various factors, e.g., their sweetening power, any applicable regulatory provisions of the country where the beverage product is to be marketed, the desired level of sweetness of the beverage product, etc. It will be within the ability of those skilled in the art, given the benefit of this disclosure, to select suitable additional or alternative sweeteners for use in various embodiments of the beverage products and formulations disclosed here.

As mentioned above, at least certain exemplary embodiments of the beverage products and formulations disclosed here may employ a steviol glycoside, a rebaudioside, *Stevia rebaudiana* extract or related compounds for sweetening. *Stevia* (e.g., *Stevia rebaudiana* Bertoni) is a sweet-tasting plant with leaves containing a complex mixture of naturally sweet diterpene glycosides. These sweeteners can be obtained, for example, by extraction or various other methods known in the art. Typically, these sweetening compounds are found to include, for example, stevioside, steviolbioside, the rebaudiosides (including, e.g., rebaudioside A, rebaudioside B, rebaudioside C, rebaudioside D, and rebaudioside E), and dulcoside A. In certain exemplary and non-limiting embodiments, a sweetener derived from Stevia is included in the beverage product in an amount between about 0.005%-1.00% by weight, e.g., between about 0.05%-1.0%, or between about 0.5%-1.0%.

The sweetener Lo Han Guo, which has various different spellings and pronunciations and is abbreviated here in some instances as LHG, can be obtained from fruit of the plant family Cucurbitaceae, tribe Jollifieae, subtribe Thladianthinae, genus *Siraitia*. LHG often is obtained from the genus/species *S. grosvenorii, S. siamensis, S. silomaradjae, S. sikkimensis, S. africana, S. borneensis*, and *S. taiwaniana*. Suitable fruit includes that of the genus/species *S. grosvenorii*, which is often called Luo Han Guo fruit. LHG contains triterpene glycosides or mogrosides, which constituents may be used as LHG sweeteners. Lo Han Guo is a potent sweetener which can be provided as a natural nutritive or natural non-nutritive sweetener. For example. Lo Han Guo juice concentrate may be a nutritive sweetener, and Lo Han Guo powder may be a non-nutritive sweetener. In certain exemplary and non-limiting embodiments, Luo Han Guo can be used as the juice or juice concentrate, powder, etc. LHG juice may include at least about 0.1% (e.g., from 0.1% to about 15%), mogrosides (e.g., mogroside V, mogroside IV, II-oxo-mogroside V), siamenoside and mixtures of any of them. In certain exemplary embodiments, Mogroside V derived from LHG can be used as a natural non-nutritive sweetener. LHG can be produced, for example, as discussed in U.S. Pat. No. 5,411,755. Sweeteners from other fruits, vegetables or plants also may be used as natural or processed sweeteners or sweetness enhancers in certain exemplary embodiments of the beverage products and formulations disclosed here.

As used here, a "non-nutritive sweetener" is one which does not provide significant caloric content in typical usage amounts, i.e., is one which imparts less than 5 calories per 8 oz. serving of beverage product to achieve the sweetness equivalent of 10 Brix of sugar. Typically, Brix tables are used in the beverage industry to determine sugar content of a particular composition. The Brix level can be measured using any suitable technology, such as a refractometer, hydrometer, and the like. The Brix measurement defines the ratio of sugar to water and does not take into account the specific gravity of the composition. As used here, "reduced calorie beverage product" means a beverage product having at least a 25% reduction in calories per 8 oz. serving of beverage product as compared to the full calorie version, typically a previously commercialized full-calorie version. As used here, a "light beverage product" means a beverage product having at least ⅓ less calories per 8 oz. serving of beverage product as compared to the full calorie version, typically a previously commercialized full-calorie version. As used here, a "low-calorie beverage product" has fewer than 40 calories per 8 oz. serving of beverage product. In certain exemplary embodiments, the beverage product or formulation disclosed here is a light orange juice beverage product having about 50 calories per 8 oz. serving.

In certain exemplary and non-limiting embodiments, additional ingredients may be added to the beverage products and formulations disclosed here. These additional ingredients may also be referred to as food or beverage ingredients and include, but are not limited to, acidulants, colorants, flavorants, minerals, vitamins, fruit juices, fruit flavors, or other fruit products, other taste modifiers (e.g., tastants, masking agents and the like), flavor enhancers, buffering agents (e.g., the sodium and potassium salts of citric, tartaric, lactic acids and the like), preservatives (e.g., benzoates, sorbates and the like), salts, thickeners, and anti-foaming agents, any of which typically can be added alone or in combination to various beverage products or formulations to vary the taste, mouthfeel, nutritional characteristics, etc. Carbonation in the form of carbon dioxide may be added for effervescence. Optionally, caffeine can be added. Additional and alternative suitable ingredients will be recognized by those skilled in the art given the benefit of this disclosure.

In certain exemplary and non-limiting embodiments, the beverage products and formulations disclosed here comprise an acidulant as an additional beverage ingredient. Suitable acidulants include, but are not limited to, organic acids, sodium benzoate, metal bisulfates, and the like or combinations thereof. Organic acids used in certain exemplary and non-limiting embodiments of the beverage products and formulations disclosed here can serve one or more additional functions, including, for example, lending tartness to the taste of the beverage product or formulation, enhancing palatability, increasing thirst quenching effect, acting as a mild preservative, etc. Exemplary organic acids include, but are not limited to, citric acid, malic acid, ascorbic acid, tartaric acid, lactic acid, adipic acid, fumaric acid, gluconic acid, succinic acid, maleic acid, and the like or combinations thereof. Other suitable acids are known and will be apparent to those skilled in the art given the benefit of this disclosure. The particular acid or acids chosen and the amount used will depend, in part, on the other ingredients, the desired shelf life of the beverage product or formulation, as well as effects on the beverage product or formulation pH level, titratable acidity, taste, and the like. It will be within the ability of those skilled in the art, given the benefit of this disclosure, to select a suitable acid or combination of acids and the amount of acids necessary for the acidulant component of any particular embodiment of the beverage products or formulations disclosed here. For example, certain embodiments of the beverage product or formulation may include one or more organic acids in an amount from about 0.1% to about 1.0% by weight of the beverage product, e.g., about 0.2% to about 0.7% by weight, or about 0.3% to about 0.6%, or about 0.7% to about 0.8% by weight.

In certain exemplary and non-limiting embodiments, the beverage products and formulations disclosed here comprise a colorant as an additional beverage ingredient. As used here, the "colorant" is intended to mean any compound that imparts color, and includes, but is not limited to, a natural pigment, a synthetic pigment, a color additive, and the like or mixtures of any of them. Both natural and artificial colors may be used. One or more FD&C dyes (e.g., yellow #5, blue #2, red #40, etc.) and/or FD&C lakes can be used for coloring solutions, food or beverage products, or compositions disclosed here. Exemplary lake dyes include, but are not limited to, FDA-approved Lake (e.g., Lake red #40, yellow #6, blue #1, and the like or mixtures of any of them). Additionally, a mixture of FD&C dyes or a FD&C lake dye in combination with other conventional food and food colorants may be used. Examples of other suitable coloring agents, include, but are not limited to, natural agents, fruit and vegetable juices and/or powders, caramel color, riboflavin, carotenoids (for example, beta-carotene), tumeric, lycopenes, and the like or combinations thereof. The exact amount of coloring agent used will vary, depending on the agents used and the intensity desired in the finished product. Generally, if included, the coloring agent should be present at a level of from about 0.0001% to about 0.5%, from about 0.001% to about 0.1%, or from about 0.004% to about 0.1%, by weight or volume of the beverage product or formulation. Additional and alternative colorants and their respective required amounts will be recognized by those skilled in the art given the benefit of this disclosure.

In certain exemplary and nonlimiting embodiments, the beverage products and formulations disclosed here comprise a flavorant as an additional beverage ingredient. Flavorants include, e.g., fruit flavors, botanical flavors, spice flavors, taste modifiers, and the like. Flavorants can be in the form of an extract, essential oil, oleoresin, juice concentrate, bottler's base, or other forms known in the art. In certain exemplary embodiments, spice or other flavors compliment that of a juice or juice combination. Exemplary flavorants suitable for use include cola flavor, tea flavor, citrus flavor, berry flavor, spice flavor, and the like or combinations thereof. In certain exemplary embodiments disclosed here, the flavorant can be present at a concentration of from about 0% to about 0.400% by weight of the final food or beverage product (e.g., from about 0.050% to about 0.200%, from about 0.080% to about 0.150%, from about 0.090% to about 0.120% by weight). Additional and alternative suitable flavorants and their respective required amounts will be recognized by those skilled in the art given the benefit of this disclosure.

In certain exemplary and non-limiting embodiments, the beverage products and formulations disclosed here comprise a desired amount of one or more fruit flavors as an additional beverage ingredient. As used here and in the appended claims, the term "fruit flavor" refers to any fruit fraction, fruit component (e.g., rind, zest, pith, pericarp, pulp, flower (e.g., petals), leaf, stem, seed, and the like), from the named fruit (FTNF) flavor (e.g., a combination of fruit essence, fruit oil and/or fruit flavor (e.g., an orange from the named fruit flavor, etc.), fruit extract (e.g., expressed, absorbed, macerated, distilled and the like), fruit oil (e.g., essential oil, folded essential oil, etc.), fruit essence, fruit puree, fruit aroma, and the like or combinations thereof that can be added to a food or beverage product to enhance flavor (e.g., to provide and/or enhance one or more high note flavors). Fruit flavors include, but are not limited to, flavors derived from orange, (e.g., mandarin, blood., navel, Valencia, etc.), tangerine, tangelo, minneola, kumquat, clementine, grapefruit, lemon, rough lemon, lime, leech lime, pummelo, pomelo, apple, grape, pear, peach, nectarine, apricot, plum, prune, pomegranate, blackberry, blueberry, raspberry, strawberry, cherry, cranberry, currant, gooseberry, boysenberry, huckleberry, mulberry, date, pineapple, banana, papaya, mango, lychee, passionfruit, coconut, guava, kiwi, watermelon, cantaloupe, honeydew melon, and the like or combinations of any of them (e.g., fruit punch). In certain exemplary embodiments, one or more citrus fruit flavors are used. The citrus flavor may include one or more of an orange fraction, an orange component, an orange extract, an orange essential oil, an orange folded essential oil, an orange aroma, an orange essence, and the like or combinations thereof. The citrus flavor may also include one or more of a fraction, component, extract, essential oil, folded essential oil, aroma, or essence of grapefruit, lemon, lime, or tangerine, among others. The citrus flavor may also include chemical compounds extracted from natural sources or synthetically produced (e.g., limonene, octanol and its derivatives, acetaldehyde, α-pinene, β-pinene, sabinene, myrcene, octanal, linalool, carene, decanal, citral, sinensal, and the like). In certain exemplary embodiments, the fruit flavor is present in an amount from about 0.001% to about 0.005% by weight of the beverage product or formulation, from about 0.01% to about 0.05% by weight, or in an amount of approximately about 0.01% to about 0.5% by weight. Additional and alternative suitable fruit flavors and their respective required amounts will be recognized by those skilled in the art given the benefit of this disclosure.

In certain exemplary and non-limiting embodiments, the beverage products and formulations disclosed here comprise a botanical flavor as an additional beverage ingredient. As used here and in the appended claims, the term "botanical flavor" refers to flavors derived from parts of a plant other than the fruit. As such, botanical flavors can include those flavors derived from essential oils and extracts of nuts, bark, roots and leaves. Examples of such flavors include, but are not limited to, cola flavors, tea flavors, spice flavors, and the like or mixtures of any of them. Additional and alternative suitable botanical flavors will be recognized by those skilled in the art given the benefit of this disclosure.

In certain exemplary and non-limiting embodiments, the beverage products and formulations disclosed here comprise a spice flavor as an additional beverage ingredient. Non-limiting examples of spice flavors include cassia, clove, cinnamon, pepper, ginger, vanilla, cardamom, coriander, root beer, sassafras, ginseng, and others. In certain exemplary embodiments disclosed here, such spice or other flavors compliment that of a fruit flavor. Additional and alternative suitable spice flavors will be recognized by those skilled in the art given the benefit of this disclosure.

In certain exemplary and non-limiting embodiments, the beverage products and formulations disclosed here comprise a taste modifier as an additional beverage ingredient. Taste modifiers may provide their own characteristic flavor, or may have little or no flavor impact by themselves. Taste modifiers have any one or more of the properties of reducing, masking, or eliminating undesirable taste characteristics, or enhancing desirable taste characteristics, for example, by controlling one or more of sweetness, sourness, bitterness, saltiness, mouthfeel, or taste temporal effects. Non-limiting examples of undesirable taste characteristics reduced by taste modifiers include one or more of bitter aftertaste, metallic aftertaste, astringency, thin mouthfeel, harshness, delayed sweetness onset, lingering sweetness, excess sourness, and other off-notes. Non-limiting examples of desirable taste characteristics enhanced by taste modifiers include one or more of sweetness intensity or impact, fullness or body, and smoothness, among others. Non-limiting examples of taste modifiers include, but are not limited to, organic acids (e.g., citric acid, malic acid, ascorbic acid, tartaric acid, lactic acid, adipic acid, fumaric acid, gluconic acid, succinic acid, maleic acid, among others), propylene glycol, glycerol, ethanol, commercially available products (e.g., Symrise™ Natural Flavor, Sweetness Enhancer Type SWL 196650, Firmenich Natural Flavor (Modulasense™ Type) 560249 T, and Firmenich™ Natural Flavor (Modularome™ Type) 539612 T, etc.), and the like or combinations thereof. It will be within the ability of those skilled in the art, given the benefit of this disclosure, to select suitable additional or alternative taste modifiers for use in various embodiments of the beverage products and formulations disclosed here.

In certain exemplary and non-limiting embodiments of the beverage products and formulations disclosed here, the one or more flavorants can be used in the form of an emulsion. A flavoring emulsion can be prepared by mixing some or all of the flavorings together, optionally together with other ingredients of the beverage product, and an emulsifying agent. The emulsifying agent may be added with or after the flavoring agents are mixed together. In certain exemplary embodiments the emulsifying agent is water-soluble. Exemplary and non-limiting examples of suitable emulsifying agents include gum acacia, modified starch, carboxymethylcellulose, gum tragacanth, gum ghatti, other suitable gums, etc. Additional suitable emulsifying agents will be apparent to those skilled in the art of beverage formulations, given the benefit of this disclosure. The emulsifier in exemplary embodiments comprises greater than about 3% by weight of the mixture of flavoring agent and emulsifier. In certain exemplary embodiments the emulsifier is from about 5% to about 30% of the mixture. It will be within the ability of those skilled in the art, given the benefit of this disclosure, to select suitable amounts of emulsifier for use in various embodiments of the beverage products and formulations disclosed here.

Weighting agents, which can also act as clouding agents, are typically used to keep the emulsion droplets dispersed in the beverage. Examples of such weighting agents include, but are not limited to, brominated vegetable oils, rosin esters, ester gums, and the like or combinations thereof. Common commercially available weighting agents are suitable for use in the beverage products and formulations disclosed here. Besides weighting agents, emulsifiers and emulsion stabilizers can be used to stabilize the flavor emulsion droplets. Examples of such emulsifiers and emulsion stabilizers include, but are not limited to, gums, pectins, cellulose, polysorbates, sorbitan esters, propylene glycol alginates, and the like or combinations thereof.

In certain exemplary and non-limiting embodiments, the beverage product or formulation disclosed here comprises carbon dioxide as an additional ingredient. Carbon dioxide is used to provide effervescence to certain exemplary embodiments of the beverage products and formulations disclosed here. Any of the techniques and carbonating equipment known in the art for carbonating beverages can be employed. Carbon dioxide can enhance the beverage taste and appearance and can aid in safeguarding the beverage purity by inhibiting and destroying objectionable bacteria. In certain embodiments, for example, the beverage product or formulation has a $CO_2$ level up to about 7.0 volumes carbon dioxide. Typical embodiments may have, for example, from about 0.5 to 5.0 volumes of carbon dioxide. As used here and independent claims, one volume of carbon dioxide is defined as the amount of carbon dioxide absorbed by any given quantity of water at 60° F. (16° C.) temperature and atmospheric pressure. A volume of gas occupies the same space as does the water by which it is absorbed. The carbon dioxide content can be selected by those skilled in the art based on the desired level of effervescence and the impact of the carbon dioxide on the taste or mouthfeel of the beverage product or formulation.

In certain exemplary and non-limiting embodiments, the beverage product or formulation comprises caffeine as an additional beverage ingredient. The amount of caffeine added is determined by the desired beverage product or formulation properties, any applicable regulatory provisions of the country where the beverage product or formulation is to be marketed, etc. The caffeine must be of purity acceptable for use in foods and beverages. The caffeine can be natural (e.g., from kola, cocoa nuts, coffee and/or tea) or synthetic in origin. In certain embodiments, the amount of caffeine can be from about 0.002% to about 0.05% by weight of the beverage product or formulation. In certain embodiments, the amount of caffeine is from about 0.005% to about 0.02% by weight of the beverage product. In certain embodiments caffeine is included at a level of 0.02% or less by weight of the beverage product. For concentrates or syrups, the caffeine level can be from about 0.006% to about 0.15%. Caffeine levels can be higher, for example, if flavored coffees which have not been decaffeinated are used since these materials contain caffeine naturally. It will be within the ability of those skilled in the art, given the benefit of this disclosure, to select suitable amounts of caffeine for use in various embodiments of the beverage products and formulations disclosed here.

In certain exemplary embodiments, the beverage products and formulations disclosed here are natural in that they do not contain anything artificial or synthetic that would not normally be expected to be in food. In certain exemplary embodiments, the beverage products and formulations disclosed here do not contain any artificial sweeteners. In certain exemplary embodiments, the beverage products and formulations disclosed here are naturally sweetened with a natural non-nutritive sweetener. As used here, a "natural" beverage ingredient is defined in accordance with the following guidelines: Raw materials for a natural ingredient exists or originates in nature. Biological synthesis involving fermentation and enzymes can be employed, but synthesis with chemical reagents is not utilized. Artificial colors, preservatives, and flavors are not considered natural ingredients. Ingredients may be processed or purified through certain specified techniques, e.g., physical processes, fermentation, enzymolysis etc. Appropriate processes and purification techniques include, but are not limited to, absorption, adsorption, agglomeration, centrifugation, chopping, cooking (e.g., baking, frying, boiling, roasting, etc.), cooling, cutting, chromatography, coating, crystallization, digestion, drying (e.g., spray, freeze drying, vacuum, etc.), evaporation, distillation, electrophoresis, emulsification, encapsulation, extraction, extrusion, filtration, fermentation, grinding, infusion, maceration, microbiological (e.g., rennet, enzymes), mixing, peeling, percolation, refrigeration/freezing, squeezing, steeping, washing, heating, mixing, ion exchange, lyophilization, osmosis, precipitation, salting out, sublimation, ultrasonic treatment, concentration, flocculation, homogenization, reconstitution, enzymolysis (e.g., using enzymes found in nature), and the like or combinations thereof. Processing aids (currently defined as substances used as manufacturing aids to enhance the appeal or utility of a food component, including clarifying agents, catalysts, flocculants, filter aids, and crystallization inhibitors, etc. See 21 CFR § 170.3 (o)(24)) are considered incidental additives and may be used if removed appropriately.

In certain exemplary and non-limiting embodiments, the beverage products and formulations disclosed here comprise a mineral as an additional beverage ingredient. Suitable minerals include, but are not limited to, added calcium, chloride, chromium, potassium, magnesium, phosphorous, sodium, sulfur, cobalt, copper, fluorine, iodine, manganese, molybdenum, nickel, selenium, vanadium, zinc, iron, and the like or combinations thereof. The minerals may be added in any form compatible with human nutritional requirements and may be added to any desired level. The amounts in the beverage product or formulation may be at any suitable percentage of the Reference Daily Intake (RDI). For example, the mineral may be present at an upper limit of about: 2%, 5%, 10%, 20%, 25%, 30%, 40%, 50%, 60%, 75%, 100%, 150%, 200%, 300%, 400%, or about 500% of the RDI. The mineral may be present at a lower limit of about: 1%, 2%, 5%, 10%, 20%, 25%, 30%, 40%, 50%, 60%, 75%, 100%, 150%, 200%, or about 300% of the RDI. Alternatively, the amount of added mineral may be measured in international units (IU) or weight/weight (w/w). It should be understood that the term "added" (e.g., "added calcium") as used here and in the appended claims refers to an added component obtained from external sources and does not include a component that is inherently present in the beverage product or formulation. For example, "added calcium" as used here and in the appended claims means that the calcium is obtained from external sources and does not include calcium that is inherent in the beverage product or formulation. Suitable added minerals for the beverage products and formulations disclosed here can be derived from any known or otherwise effective nutrient source that provides the targeted mineral separately. For example added calcium sources include, but are not limited to, e.g., calcium citrate, calcium phosphate, or any other calcium source suitable for use in a beverage product or formulation.

In certain exemplary and non-limiting embodiments, the beverage products and formulations disclosed here comprise a vitamin as an additional beverage ingredient. Suitable vitamins include, but are not limited to, added Vitamin A (including Vitamin A precursors, e.g., beta carotene), Vitamin $B_1$ (i.e., thiamine), Vitamin $B_2$ (i.e., riboflavin), Vitamin $B_3$ (i.e., niacin), Vitamin $B_6$, Vitamin $B_7$ (i.e., biotin), Vitamin $B_9$ (i.e., folic acid), Vitamin $B_{12}$ (i.e., cobalamin), Vitamin C (i.e., ascorbic acid), Vitamin D, and Vitamin E (i.e., tocopherols and tocotrienols), and Vitamin K, and the like or combinations thereof. The vitamins may be added in any form compatible with human nutritional requirements and may be added to any desired level. The amounts in the beverage product or formulation may be at any suitable percentage of the Reference Daily Intake (RDI). For example, the vitamin may be present at an upper limit of about: 2%, 5%, 10%, 20%, 25%, 30%, 40%, 50%, 60%, 75%, 100%, 150%, 200%, 300%, 400%, or about 500% of the RDI. The vitamin may be present at a lower limit of about: 1%, 2%, 5%, 10%, 20%, 25%, 30%, 40%, 50%, 60%, 75%, 100%, 150%, 200%, or about 300% of the RDI. Alternatively, the amount of added vitamin may be measured in international units (IU) or weight/weight (w/w). For example, a beverage product serving may contain 100% of the RDI of each of Vitamin E, Vitamin B3 (niacin), Vitamin B5 (pantothenic acid), Vitamin B6, and Vitamin B12. Suitable added vitamins for the beverage products and formulations disclosed here can be derived from any known or otherwise effective nutrient source that provides the targeted vitamin separately.

In certain exemplary and non-limiting embodiments the beverage products and formulations disclosed here include homogenized pulp. Homogenized pulp enhances the mouthfeel of the beverage product or formulation by providing increased viscosity. In addition, homogenized pulp provides added fruit flavor (e.g., orange flavor from orange pulp), and added sweetness to the beverage product or formulation. In certain exemplary embodiments, homogenized pulp comprises citrus pulp, e.g., orange pulp, grapefruit pulp, lemon pulp, lime pulp, among others, and mixtures of any of them. As used here, citrus pulp is defined as the ruptured juice sacs and segment walls recovered after the citrus juice extraction process. As used here, "homogenized pulp" is defined as pulp particles suspended in aqueous solution that do not separate out of suspension. Homogenized pulp may be produced by various homogenization techniques, using equipment e.g., a blender or a colloid mill. In certain exemplary embodiments, the homogenized pulp has an average particle size of about 60 to about 200 microns in diameter, about 70 to about 100 microns, or about 150 to about 250 microns; where at least 80% of the homogenized pulp particles are between 50 and 540 microns in diameter. In certain exemplary embodiments, the beverage product or formulation includes homogenized pulp in an amount from about 5% to about 20% by weight of the beverage product or formulation, e.g., about 10% to about 15% by weight.

Optionally, additional ingredients known or expected to have beneficial effects may be added. For example, the beverage product or formulation may contain one or more of the following: oils (e.g., omega-3, omega-6, etc.), herbs and spices. The herbs and spice ingredients may be in extracted form. Any suitable herb and spice known in the art may be used as an ingredient. Exemplary herbs and spices that may be added include, but are not limited to, Kava Kava, St. John's Wort, Saw Palmetto, ginseng, and the like.

In certain exemplary and non-limiting embodiments disclosed here, the beverage products and formulation disclosed here comprise at least one buffering agent as an additional beverage ingredient. Buffering agents are typically used to adjust pH. Such pH adjusters include, but are not limited to, the sodium or potassium salts of citric, tartaric, malic, fumaric, cinnamic, maleic, adipic, glutaric, lactic, and succinic acid, or any combination of them. The amount of buffering agent included will depend, of course, on the type of buffering agents and on the degree to which the pH is to be adjusted. Additional and alternative buffering agents and their respective required amounts will be recognized by those skilled in the art given the benefit of this disclosure.

In certain exemplary and non-limiting embodiments, the beverage product or formulation disclosed here have a pH with a lower limit of about 2.6, about 2.75, about 3.0, about 3.2, about 3.5, about 3.6, about 3.75, about 3.8, or about 4.0 and an upper limit of about 3.6, about 3.8, about 4.0, about 4.2, or about 4.5. In certain exemplary embodiments, the pH range is 3.4 to 4.0. In certain exemplary embodiments, the pH is at most 4.5.

In certain exemplary and non-limiting embodiments, the beverage product or formulation disclosed here comprises salt as an additional ingredient. Salts can act as a flavor potentiator and the amount used will vary, depending on the salt used and the intensity desired in the finished product. Suitable examples include, but are not limited to, alkali or alkaline earth metal chlorides (e.g., potassium chloride, sodium chloride, calcium chloride, magnesium chloride etc.), glutamates, (e.g., monosodium glutamate) and the like or combinations thereof.

In certain exemplary and non-limiting embodiments, the beverage product or formulation disclosed here comprises a thickener as an additional ingredient. As referred to here, "thickener" may include any material which increases the viscosity or increases the cream-like mouthfeel of the beverage product or formulation. Examples of suitable thickeners for use in the beverage products and formulations disclosed here include, but are not limited to, carbohydrates, proteins, fats, lipids, hydrocolloids, gums, and the like or combinations thereof. In certain embodiments, the thickener may comprise gum arabic, gum karaya, gum tragacanth, gum ghatti, agar-agar, guar gum, locust bean gum, konjac, alginates, carrageenans, pectin, tara gum, xanthan gum, gellan gum, pullulan, curdlan, cellulose, microcrystalline cellulose, carboxymethylcellulose gum, gelatin, chitosan, maltodextrin, or combinations thereof.

In certain exemplary and non-limiting embodiments, the beverage product or formulation disclosed here comprises an anti-foaming agent as an additional ingredient. Examples of suitable anti-foam agents for use in the beverage products and formulations disclosed here include, but are not limited to, Silicone AF-100 FG (Thompson-Hayward Chemical Co.), 'Trans' Silicone Antifoam Emulsion (Trans-Chemco, Inc.), and 1920 Powdered Antifoam (Dow Corning Chemical). The amount of the anti-foam agent used is determined by the minimum amount required to prevent excessive foaming during processing of the beverage product or formulation and, if desired by the consumer of the beverage product or formulation, to prevent excessive foaming during processing of the food or beverage product into which the product is being incorporated. Additional suitable anti-foaming agents will be apparent to those skilled in the art of beverage formulations, given the benefit of this disclosure.

In certain exemplary and non-limiting embodiments, the beverage product or formulation disclosed here comprises an aroma chemical as an additional ingredient. In certain exemplary embodiments, the aroma chemical may include any chemical designated by the Flavor and Extract Manufacturers' Association (FEMA) to be Generally Recognized As Safe (GRAS). A chemical designated as GRAS by FEMA has been tested using certain standards and deemed safe for use by humans. Exemplary GRAS aroma chemicals include, but are not limited to acetic aldehyde, acetic acid, Isoamyl acetate, 3-methylbutanol, isoamyl butyrate, isoamyl hexanoate, isoamyl isovalerate, benzaldehyde, benzoic acid, benzyl acetate, benzyl alcohol, benzyl cinnamate, butyl acetate, isobutyl acetate, butanol, isobutanol, butyl butyrate, isobutyl butyrate, butyl isobutyrate, butyl hexanoate, isobutyl propionate, butyraldehyde, isobutyraldehyde, butyric acid, isobutyric acid, cinnamaldehyde, cinnamic acid, 2,3-butanedione, ethyl acetate, ethyl acetoacetate, ethyl benzoylacetate, ethyl butyrate, ethyl isobutyrate, ethyl cinnamate, ethyl heptanoate, ethyl hexanoate, ethyl lactate, ethyl 2-methylbutyrate, ethyl propionate, ethyl pyruvate, ethyl valerate, ethyl isovalerate, 2-heptanone, hexanal, hexanoic acid, hexanol, raspberry ketone, α-ionone, β-ionone, lactic acid, 2-methylbutyraldehyde, isovaleraldehyde, 2-methylbutyric acid, methyl cinnamate, methyl 2-methylbutyrate, methyl propionate, propionaldehyde, propanoic acid, propanol, pyruvic acid, valeric acid, isovaleric acid, vanillin, 4-methyl-5-hydroxyethyl thiazole, acetone, heptanoic acid, 2-methylbutyl 2-methylbutyrate, 2-isopropyl-5-methyl-2-hexenal, ethyl 3-hydroxybutyrate, 2-methylbutyl isovalerate, isoamyl isobutyrate, tiglic acid, D-2-methylbutyl acetate, L-2-methylbutanol, methanol, cyclopentadecanone, acetic anhydride, and other compounds. GRAS aroma chemicals may be extracted from natural sources or produced synthetically. It will be within the ability of those skilled in the art, given the benefit of this disclosure, to select a suitable aroma chemical or combination of aroma chemicals suitable for use in the beverage products and formulations according to this disclosure.

In certain exemplary and non-limiting embodiments, the beverage product or formulation disclosed here comprises a preservative as an additional ingredient. That is, at least certain exemplary embodiments contain an optional dissolved preservative system. Solutions with a pH below 4 and especially those below 3 typically are "microstable," i.e., they resist growth of microorganisms, and so are suitable for longer term storage prior to consumption without the need for further preservatives. However, an additional preservative system can be used if desired. If a preservative system is used, it can be added to the beverage product at any suitable time during production, e.g., in some cases prior to the addition of the sweetener. As used here, the terms "preservation system" or "preservatives" include all suitable preservatives approved for use in food and beverage compositions, including, without limitation, such known chemical preservatives as benzoates, e.g., sodium, calcium, and potassium benzoate, sorbates, e.g., sodium, calcium, and potassium sorbate, citrates, e.g., sodium citrate and potassium citrate, polyphosphates, e.g., sodium hexametaphosphate (SHMP), and mixtures thereof, and antioxidants e.g., ascorbic acid, EDTA, BHA, BHT, TBHQ, dehydroacetic acid, dimethyldicarbonate, ethoxyquin, heptylparaben, etc. Other suitable preservatives for use in the beverage products and formulations disclosed here include natural preservatives, e.g., nisin, cinnamic acid, grape pomace extract, salt, vinegar, and the like. It will be within the ability of those skilled in the art, given the benefit of this disclosure, to select a suitable aroma preservative or combination of preservatives suitable for use in the beverage products and formulations according to this disclosure.

Preservatives can be used in amounts not exceeding mandated maximum levels under applicable laws and regulations. The level of preservative used typically is adjusted according to the planned final product pH, as well as an evaluation of the microbiological spoilage potential of the particular beverage formulation. The maximum level employed typically is about 0.05% by weight of the beverage product or formulation. It will be within the ability of those skilled in the art, given the benefit of this disclosure, to select a suitable amount of preservative for beverage products and formulations according to this disclosure.

Certain exemplary methods, beverage products and formulations in accordance with the disclosure are described in greater detail in the examples presented below by way of illustration.

EXAMPLES

Example 1

The use of food grade biopolymers, whey protein isolate and alginate, as encapsulating agents for probiotic bacteria was investigated. More particularly, two different ratios of whey protein isolate and alginate were studied in the manufacture of capsules comprising probiotic bacteria, and compared to capsules comprising 100% whey protein isolate or 100% alginate.

Whey Protein isolate (~60% β-lactoglobulin and 20% α-lactalburnin) was supplied by Fonterra (Palmerston North, New Zealand) and high viscosity Na-alginate (Protonal SF120) was supplied by Hawkins Watts (Auckland, New Zealand). *Lactobacillus acidophilus* ATCC 4356 was purchased from Environmental Science and Research (ESR, Wellington, New Zealand) and cultured in *Lactobacilli* MRS broth (Difco, New Zealand) at 37° C. under anaerobic conditions (GasPak EZ anaerobe container system, Becton, Dickinson and Company, USA). Activated cultures were obtained by sub-culturing 2-3 times in MRS broth for 24 hours at 37° C. before use in the experiments.

The probiotic bacteria cells ($5.4 \times 10^8$ CFU/g) cultured in 800 ml MRS broth were harvested by centrifugation at 8,500 rpm for 10 minutes at 4° C. (Hitachi High Speed Centrifuge, Massey University, Palmerston North). The pellet (~5 g) was added to sterile 0.1% peptone water (30 ml) and agitated to re-suspend the pellet. This wash step was performed twice under the same conditions. Gram staining and catalase tests were performed for confirmation of *lactobacilli*.

Bacteria were enumerated using the pour plate method with *Lactobacilli* MRS Agar (Difco). Capsules (1 g) were digested in 9 ml phosphate buffer (pH 7.1±0.1) using a stomacher for up to 30 minutes. It was not necessary for free cells to be digested. A dilution series was prepared using the digested microcapsule/phosphate buffer mixtures (or free cells) in sterile 0.1% peptone water (1 ml sample in 9 ml peptone water). Molten MRS agar was added to 1 ml of sample and plates were incubated under anaerobic conditions for 72 hours at 37° C. before colonies were counted.

$$\text{Initial dilution factor} = \frac{\text{Weight of sample}}{\text{Weight of sample} + \text{Weight of peptone}}$$

$$\text{Subsequent dilution} = \frac{\text{Volume of dilution transferred}}{\text{Volume of dilution} + \text{Volume of dilution blank}}$$

$$\text{CFU/g of sample} = \text{Colonies on plate} \times \frac{1}{\text{Initial dilution factor} \times \text{Subsequent dilutions}}$$

A 1% weight per volume (w/v) sodium alginate solution was prepared the day before experimental work and allowed to stir overnight to allow complete hydration. A 12% (w/v) whey protein isolate (WPI) solution (1000 ml) was prepared and 500 ml was heated to 90° C. for 30 min to ensure complete denaturation of proteins before being cooled to room temperature. Mixtures of alginate and WPI were prepared according to the experimental design shown in Table 1 below, and allowed to mix at room temperature for two hours to allow complete dispersion. To this solution, 2.5 ml of the cell dispersion was added to obtain a theoretical final cell concentration of $1 \times 10^{10}$ CFU/g and allowed to mix for a further 30 minutes. Samples were then incubated in a water bath at 44° C.±2° C. for 15 minutes.

TABLE 1

Experimental design for optimization of capsule materials

| Run | WPI Concentration (%) | Alginate Concentration (%) | Denaturation Step |
|---|---|---|---|
| 1 | 100 | 0 | Thermal |
| 2 | 75 | 25 | Thermal |
| 3 | 50 | 50 | Thermal |
| 4 | 0 | 100 | — |

Preparation of Microcapsules

Eighty milliliters of a 4% w/v of calcium chloride solution, used as coagulation fluid, was placed in a beaker and stirred slowly using a magnetic stirrer. Twenty milliliters of the WPI/alginate/cell dispersion mixture was fed drop-wise into the coagulation fluid. Capsules were hardened in calcium chloride for 30 minutes before being washed twice with Milli-Q water (i.e., purified and deionized water), then were stored in sterile water in sterile containers. Half the capsules were refrigerated at 4° C.±1° C. under anaerobic conditions using an anaerobic container system, and half were frozen at −21° C.±1° C. overnight before being freeze dried for 72 hours at 25° C.±2° C. Freeze dried beads were then refrigerated at 4° C.±1° C. under anaerobic conditions. All equipment was sterilized prior to use.

Capsule Morphology

The morphology of wet capsules was observed under a digital light microscope. Freeze-dried beads were also observed under Scanning Electron Microscopy (SEM, FEI Quanta 200 Scanning Electron Microscope, USA). A dissection microscope was used to select representative samples of beads which were subsequently mounted on aluminum stubs with conductive silver. Samples were then sputter-coated with gold and observed under a SEM at an accelerated voltage of 20 KV.

Example 2

Capsule Degradation Studies in Simulated Gastric and Intestinal Conditions

The behavior of both dried and wet capsules as prepared in Example 1 in simulated gastric fluid (SGF, pH 2.0) was observed, as the drying process was expected to affect the pore size and other attributes of the capsules may have influenced their stability in SGF.

SGF (pH 2±0.1) containing 0.2% NaCl, 0.7% HCl and 0.3% pepsin was prepared. Approximately 1 gram of encapsulated cells was added separately to test tubes containing 9 milliliters of SGF. Test tubes were incubated at 37° C. for 2 hours under continuous agitation (150 rpm) in a shaking water bath. A two hour incubation time was selected to represent the mean transit time through the stomach. The weight of the capsules was determined initially and then hourly up to 2 hours. Next, capsules were removed from SGF and placed in simulated intestinal fluid (SIF, pH 7.4±0.1, 37° C.) and weighed at intervals of half an hour until complete degradation was observed.

Example 3

Texture Analysis

The capsules of Example 1 were assessed for their textural characteristics using a Texture Analyzer XT-2 (TA XT-2) Plus system (Stable Micro Systems, Surrey, UK). The texture analysis was conducted with the settings as shown below in Table 2. The piston went down, keeping contact with the top of the capsules, and flattened the capsule at a constant rate of 0.2 millimeters per second (mm/s), until it reached 90% of its original height. The force exerted by the capsule as a function of displacement was recorded. The return speed of the piston to its original position after compression was 10 mm/s. The force needed for deformation was recorded as a function of time until fracturing of the capsules. A force-compression curve was obtained for each sample and stored in a file for calculation of the fracture properties using the "XT.RAD Dimension" software, version 3.7H, from Stable Micro System (Surrey, UK). From each measurement, the stress and strain at fracture were determined. The fracture stress is associated with the first peak on the graphs, representing the force as a function of displacement. For capsules, the stresses were calculated considering the contact area as the area of a sphere and assuming a dissipation of the internal beads force in all directions.

TABLE 2

Texture Analyzer XT-2 Plus settings for capsule compression tests

| Item | Setting |
|---|---|
| Test Type | Compression |
| Probe | 35 mm cylindrical probe |
| Pre-test Speed | 0.05 mm/s |
| Test Speed | 0.1 mm/s |
| Post Test Speed | 2 mm/s |
| Target Mode Strain | 50% |
| Trigger Force | 0.01N |

Example 4

Capsule Morphology

The capsules produced in Example 1 were predominantly spherical or ovoid, as shown in FIG. 1. Capsules produced from pure alginate were regular and spherical; however, as the whey protein content increased, microcapsules became more ovoid and irregular. The surface of the wet capsules appeared to be variable, with pure WPI capsules displaying an uneven ridged surface, as shown in FIG. 1A, and alginate beads displaying a smoother surface (not shown). However, the digital microscope technique could not detect other surface characteristics such as porosity and cavities. FIG. 1B includes a scale bar having a length of 500 μm, to provide a size reference for the pictured capsule comprising a weight ratio of protein to alginate of 75:25.

The alginate capsules were white and translucent; however, as WPI content increased, the capsules became progressively more white and opaque. Without wishing to be bound by theory, this may be due to the increased number of binding sites for $Ca^{2+}$ ions as a result of the increased whey protein content, thus leading to a more densely cross-linked gel structure.

Scanning Electron Microscopy

Referring to FIG. 2, scanning electron microscope (SEM) images are provided of various freeze-dried capsules. The ovoid and spherical shape of capsules became slightly irregular following freeze-drying, as shown in FIG. 2A, which provides an image of an all WPI capsule, and in a FIG. 2B, which provides an image of a 50:50 WPI:alginate capsule. The size of the microcapsules varied with the method of whey protein denaturation and whey protein content. While many capsules were not spheres, their longest length was used to estimate their diameter. The capsule particle size was determined to have an approximate diameter of 750 μm to 1500 μm (0.75-1.5 mm), and they became larger as the WPI concentration increased.

The surface photography varied between capsules with a rougher surface observed on WPI capsules, as compared to alginate capsules. FIG. 2C shows the highly porous surface structure of freeze-dried pure WPI capsules. SEM images of alginate capsules under the same magnification did not show the same porosity; however, previous researchers have documented the presence of pores on the structure of alginate capsules (Anal et al., 2003; Anal and Stevens, 2005).

Fractured sections of freeze-dried capsules indicated the structure of the capsules consisted of a solid exterior wall covering an inner fibrous network exhibiting high porosity (not shown). Entrapped L. acidophilus cells were observed in all types of capsules and the distribution of cells entrapped in the capsules appeared to be more homogenous with cells in the interior than on the surface. FIG. 2D shows an SEM image of L. acidophilus cells observed on the surface of a freeze-dried pure WPI capsule.

Example 5

Capsule Degradation Studies in Simulated Gastric and Intestinal Conditions

One goal of embodiments of the invention was to provide capsules that are stable in SGF and degrade over a period of time in SIF, to allow for active encapsulated material to reach the colon. Literature indicates that the mean gastric emptying time is two hours and that it takes 3-4 hours following release to the duodenum for ingested particles to reach the colon (Anal, 2007).

To determine the rate at which capsules made according to Example 1 were degraded in the gastrointestinal tract, capsules were incubated in simulated gastric fluids at 37° C. The weight of the capsules was tracked over a four hour period in both SGF (pH 2.0±0.1) and SIF (pH 7.4±0.1). Referring to FIG. 3, the rate of degradation of capsules was faster in SIF than SGF for capsules made with all alginate, 75:25 WPI:alginate, and 50:50 WPI:alginate. These results likely reflect the differences in the capsules chemical behavior between the fluids. Pure WPI capsules were rapidly degraded in SGF with approximately 95% degradation after two hours of incubation. As the WPI concentration decreased and alginate concentration increased, the rate of degradation also decreased, as shown in FIG. 3.

Without wishing to be bound by theory, it is believed that the degradation behavior of WPI in SGF is mainly due to the presence of pepsin, the enzyme found in SGF. Pepsin is a proteolytic enzyme that attacks peptide bonds, causing the breakdown of the whey protein isolate and thus the capsule structure. Comparatively, 75:25 WPI:alginate capsules and 50:50 WPI:alginate capsules exhibited a slower rate of degradation in the first sixty minutes of incubation, as indicated by the graph in FIG. 3. The alginate component of the capsule may shrink in the acidic conditions to provide an effective barrier for pepsin penetration, or potentially the WPI capsules may be an easier target for pepsin attack.

The behavior of alginate in acidic conditions has been described by researchers (George and Abraham, 2006). The pKa values of mannuronic and guluronic acids, the building blocks of alginate, are 3.38 and 3.65 respectively. The pKa of the polymer itself is close to the pKa for the individual monomers and varies according to the ionic strength of the solvent and alginate concentration. However, it has been observed that at a pH below the pKa value, alginate precipitates out, believed to be as a result of depolymerization due to proton catalyzed hydrolysis.

Without wishing to be bound by theory, it is believed that in capsules made with both the food biopolymers of whey protein isolate and alginate, WPI forms capsules with the hydrophobic side chains embedded in the center of the capsule and the hydrophilic side chains facing the alginate. As pepsin may preferentially attack hydrophobic aromatic amino acids which are embedded inside the capsule, capsules containing both WPI and alginate provide protection from pepsin for the WPI. In contrast, the WPI capsules may have presented as a more vulnerable target for pepsin and hence degradation occurred more readily.

Employing the above logic, alginate capsules may have been expected to be the most stable in SGF; however, as shown in FIG. 3, this behavior was not observed. Shrinkage of the capsules, however, was observed throughout the experiment but this was in conjunction with erosion of the capsule. This is potentially due to the positively charged alginate dissociating from the $Ca^{2+}$ and allowing the gel to break down.

Figure 4:
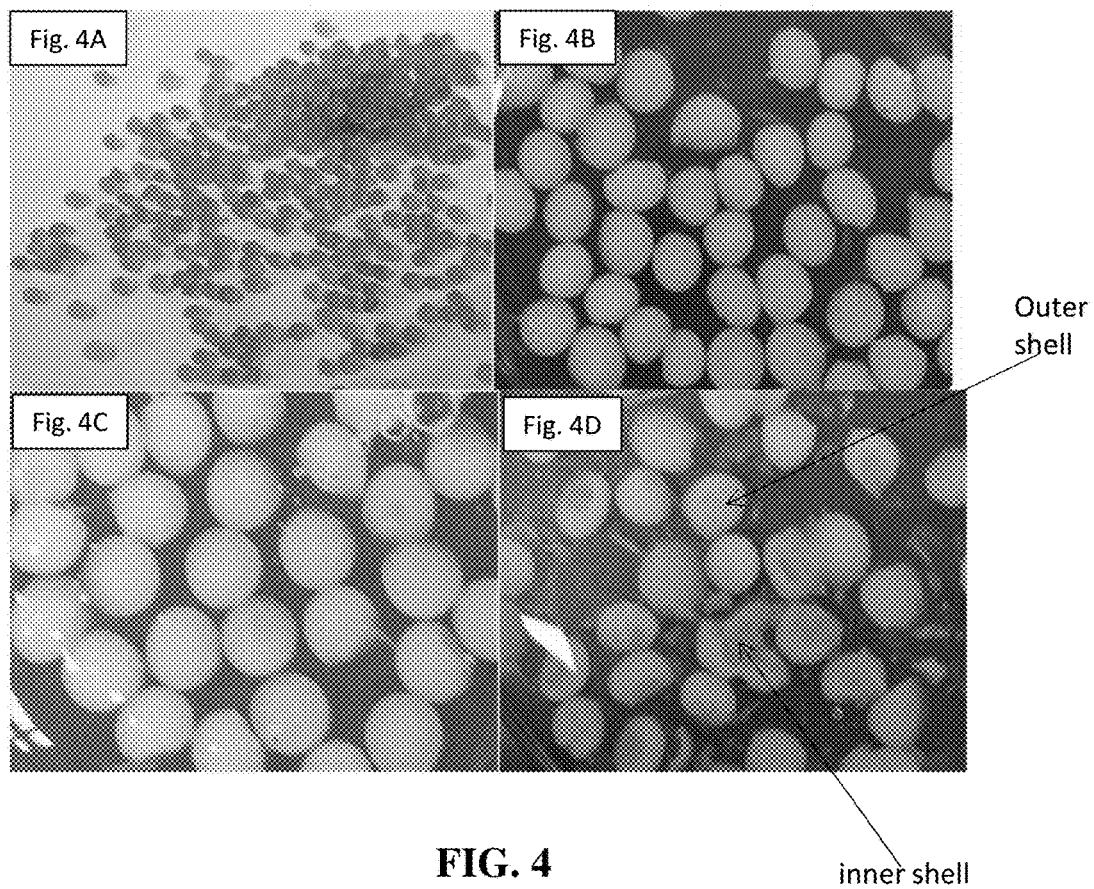
FIG. 4A depicts a photograph of dried whey protein-alginate microcapsules.
FIG. 4B depicts a photograph of whey protein-alginate microcapsules incubated in simulated gastric fluids for two hours.
FIG. 4C depicts a photograph of whey protein-alginate microcapsules incubated in simulated intestinal fluids for two hours.
FIG. 4D depicts a photograph of whey protein-alginate microcapsules incubated in simulated intestinal fluids for eight hours.

A photograph of dried microcapsules prior to incubation in simulated gastrointestinal fluids, is shown in FIG. 4A. WPI capsules, 75:25 WPI:alginate capsules and alginate capsules were rapidly degraded in SIF with 100% degradation after thirty minutes. Of the capsules, 50:50 WPI:alginate was the most stable in SIF, taking ninety minutes to degrade. As pancreatin, a proteolytic enzyme in intestinal fluid, does not degrade alginate, it might have been expected that alginate capsules would swell and form a hydrogel in SIF, leading to its degradation. Conversely, WPI capsules might have been expected to be rapidly degraded by pancreatin.

Referring to FIG. 4B, 50:50 WPI:alginate capsules were found swollen and floating after incubation in SGF for two hours, but remained intact. Upon transfer to intestinal fluid, the capsules started to disintegrate, as shown in FIG. 4C, which provides a photograph of the capsules following incubation in SIF for two hours. The disintegration of capsules was found pH-dependent. At low pH, the ionic bonds in the capsules persist, so that the gel bead matrix materials remained intact. After transfer to neutral pH, the anionic alginate in the Ca-alginate-WPI complex could be displaced by hydroxyl ions. A photograph of the capsules following incubation in SIF for eight hours is provided in FIG. 4D.

Example 6

Texture Profile Analysis

The mechanical properties of capsules define the deformation and rupture of the capsule under an external load. These properties are important when considering the protection and release of materials throughout processing and delivery systems when rupture may or may not be desired. In terms of food processing, capsules need to have considerable strength to prevent rupture when exposed to shear forces as they are moved through processing equipment. Rupture could potentially expose encapsulated bacteria to the environment where degradation and loss of bioavailability may occur.

There is limited research available on the properties of WPI:alginate capsules, which appear to have focused on the preparation methods and gastric stability of the capsules. Consequently, there is limited data on the mechanical properties of capsules. Therefore, the effects of WPI on the mechanical strength of alginate capsules have been investigated. The WPI, alginate and WPI-alginate microcapsules loaded with *L. acidophilus* were obtained by dropping a solution containing the biopolymer(s) and probiotic bacteria cells in a calcium chloride coagulation fluid. The combination of alginate and thermally-denatured WPI showed highly effective and strong capsules, capable of entrapping *L. acidophilus*.

Figure 5:
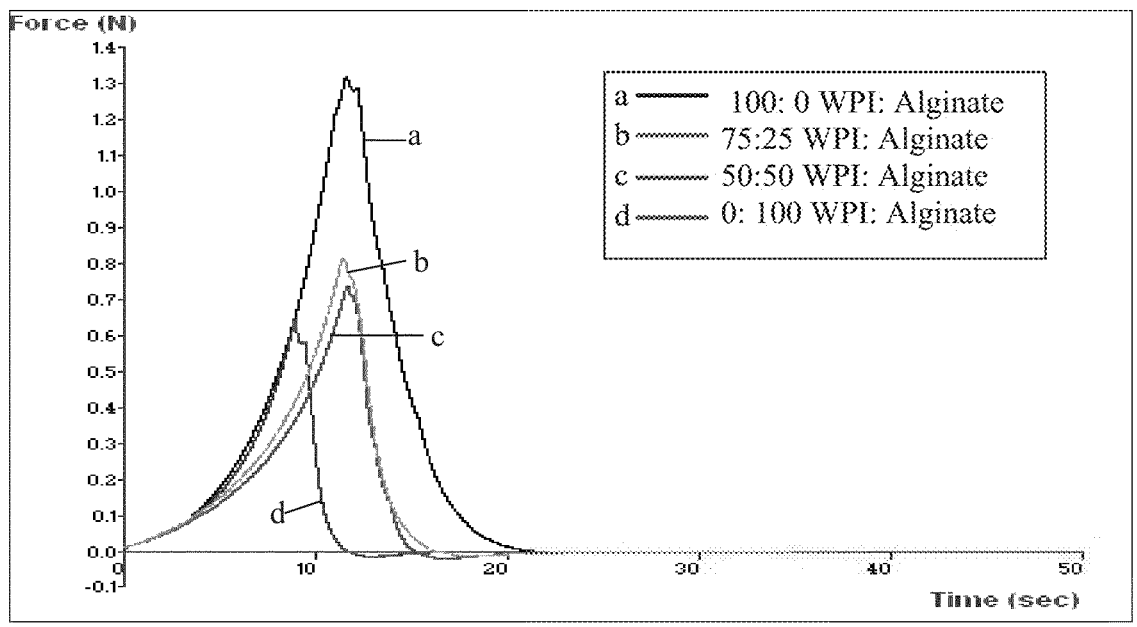
FIG. 5 depicts a force-time graph of capsules during compression of capsule height.

The mean force-time graph for the compression of the capsules is shown in FIG. 5. WPI capsules, 75:25 WPI:alginate capsules and 50:50 WPI:alginate capsules, and alginate capsules are shown. The WPI capsules and alginate capsules show more rigidity than the combination capsules (i.e., WPI:alginate capsules) as illustrated by the steeper initial slope on the graph in FIG. 5. No fracturability was observed at 50% compression and all of the tested samples showed a small amount of adhesiveness, as evident by the negative forces on the graph.

Figure 6:
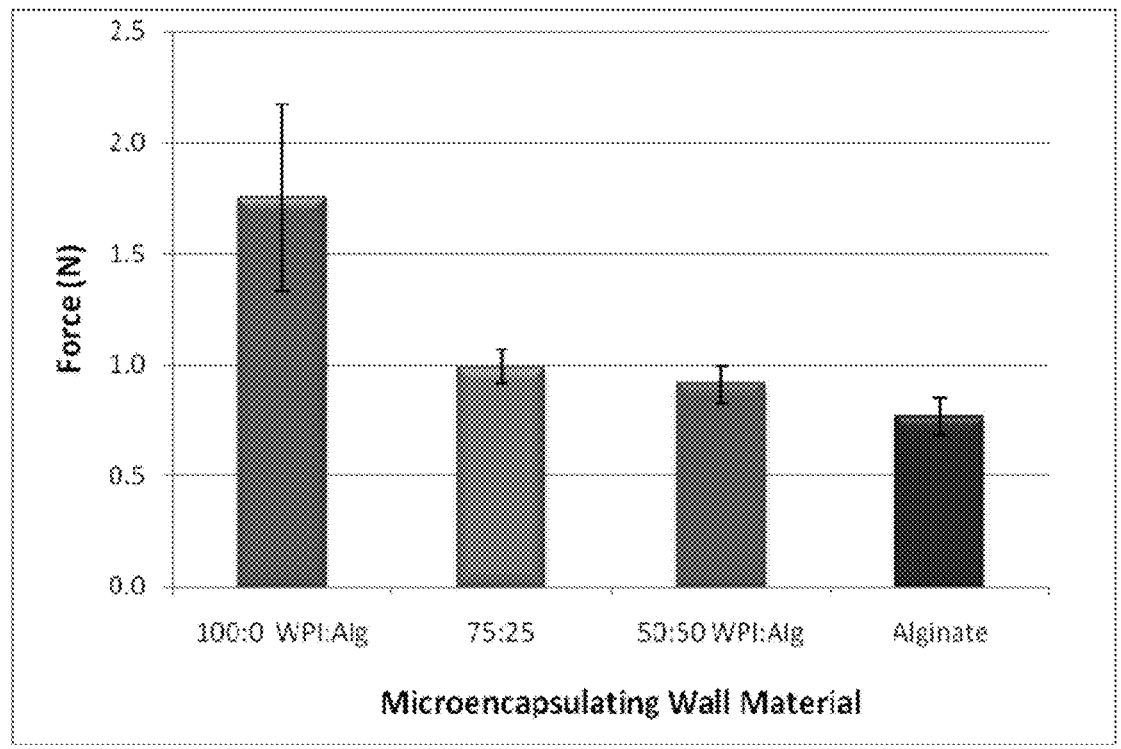
FIG. 6 depicts a peak force graph of capsules at 50% compression of total height of the capsules.

Referring now both to FIG. 5 and to FIG. 6, the peak force attained at 50% compression of the total height of the capsules is shown. Ten replicates were measured and averaged to provide the results for each capsule type shown in FIG. 6. The WPI capsules were significantly stronger than the remaining capsules, with a peak force of 1.57 N±0.2 N. The 75:25 WPI:alginate capsules attained the next highest force, of 0.99 N±0.07 N, which was not significantly different from the 50:50 WPI:alginate capsules, which had a peak force of 0.91 N±0.08 N. The weakest capsules were the alginate capsules, which had a peak force of 0.77 N±0.08 N. Therefore, as the proportion of WPI increased there was a trend toward increasing strength. This may be due to the increased number of binding sites for $Ca^{2+}$ ions, with increased WPI content.

In summary, Examples 1 through 6 showed the development of a microencapsulation system suitable for probiotic bacteria (e.g., *L. acidophilus*). This system comprises combinations of thermally denatured whey proteins and alginate as effective capsule materials. It was found that, for instance, mixtures of solutions of denatured whey protein isolate in a concentration of 12%, (w/v) and of alginate in a concentration of 1%, (w/v) in weight ratios of 3:1 and 1:1 produced effective and strong microcapsules.

Example 7

The stability of encapsulated probiotic bacteria under gastrointestinal conditions and at high temperatures was investigated in this Example. The viability and biochemical activity of *L. acidophilus* has been well documented in the literature. *L. acidophilus* does not survive well in very low pH conditions because it has an optimal pH of 4-5 (Stanton et al., 2003). When *L. acidophilus* cells pass through the gastrointestinal tract they are susceptible to damage from stomach acid and therefore fewer numbers may reach the large intestine for colonization. Accordingly, one aspect of embodiments of the invention is to provide a capsule that is resistant to digestion in the stomach, thereby protecting viable probiotic bacteria cells from the low pH environment, yet is susceptible to degradation in colonic conditions. Therefore the efficacy of the designed capsules in simulated gastric conditions was tested.

While the heat tolerance of *L. acidophilus* varies with strain, the optimal temperature for *L. acidophilus* growth is 37° C., with some strains surviving well at 50° C. Above 50° C., the survivability of cells is rapidly reduced and a lethal temperature of 60° C. has been cited in the literature (Kandler and Weiss, 1986). Currently, the application of *L. acidophilus* in probiotic preparations is limited by the organisms' intolerance to high temperatures. As a result, the efficacy of the designed capsules as a suitable thermal barrier was also investigated.

Viability of Microencapsulated and Free Cells (*L. acidophilus*) under Simulated Gastric Conditions The capsules and simulated gastric fluid (SGF) were prepared as described in Example 1. Capsules were washed in distilled water and added to 9 ml of 0.1% sterile peptone water, then refrigerated at 4° C.±1° C. overnight under anaerobic conditions. Free cells were placed into peptone water and also refrigerated overnight.

Approximately 1 gram of capsules and 1 ml of a free cell suspension were added separately to test tubes each containing 9 ml of SGF. The free cells were used as a control in the experiment. The test tubes were covered and incubated at 37° C. for two hours under continuous agitation in a shaking water bath. After one hour and two hours of incubation, samples of capsules and free cell suspensions in SGF were taken and digested the following day using a stomacher, for up to 30 minutes. Viable cell counts were then enumerated using the pour plate method.

Viability of Microencapsulated and Free Cells (*L. acidophilus*) under Heat Treatment To determine the effect of heat on the viability of microencapsulated and free *L. acidophilus*, cells were exposed to heat treatment in distilled water (pH 7.0±0.1) according to the methods described by Mandal, Puniya and Singh (2006). Specifically, the capsules and free cells were exposed to temperatures of 50° C., 60° C., or 80° C. for 20 minutes. One gram of capsules and 1 ml of fresh cells were placed in a test tube with 9 ml of distilled water. At the end of the incubation time, cells were removed and added to 9 ml of 0.1 M phosphate buffer (pH 7.1±0.1). The buffer and cell dispersion was then crushed in a stomacher until a homogenous dispersion was obtained before viable cell counts were enumerated according to Example 1. Free cells did not require this step before enumeration.

Figure 7:
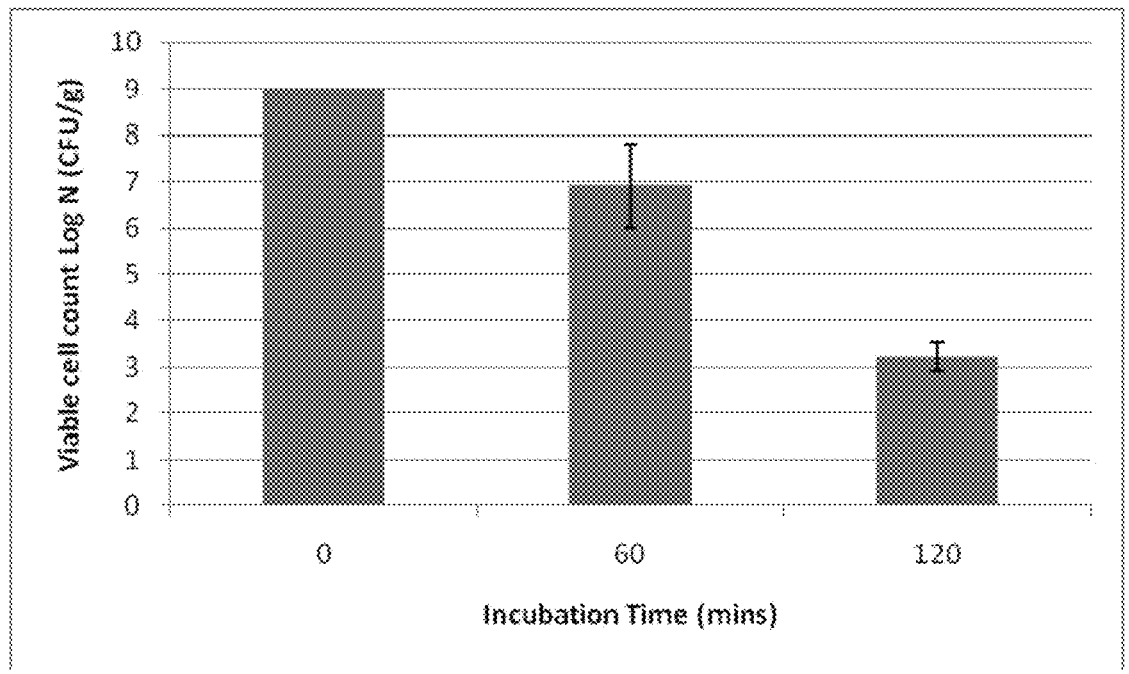
FIG. 7 depicts a graph of the viable cell count of free *L. acidophilus* cells following incubation in simulated gastric fluid and pepsin for 120 minutes.

Viability of Microencapsulated and Free Cells Under Stimulated Gastric Conditions Free Cells As shown in FIG. 7, viable counts of free (i.e., non-encapsulated) cells in simulated gastric fluid (pH 2.0±0.1, 37° C.) decreased significantly over the incubation period with a 6-log reduction from log 9 CFU/ml to log 3 CFU/ml after 120 minutes. While the pH tolerance of *L. acidophilus* varies with strain, these findings are consistent with what is generally known about *L. acidophilus* and findings reported in other studies. Krasaekoopt et al. (2004) found *L. acidophilus* cells were destroyed to the same extent with a 6-log reduction after 120 minutes (pH 1.55, 37° C.). Hood and Zottola (1988) reported that the viability of *L. acidophilus* cells decreased rapidly in pH 2 solution, with no recovery after 45 minutes.

Encapsulated Cells

Figure 8:
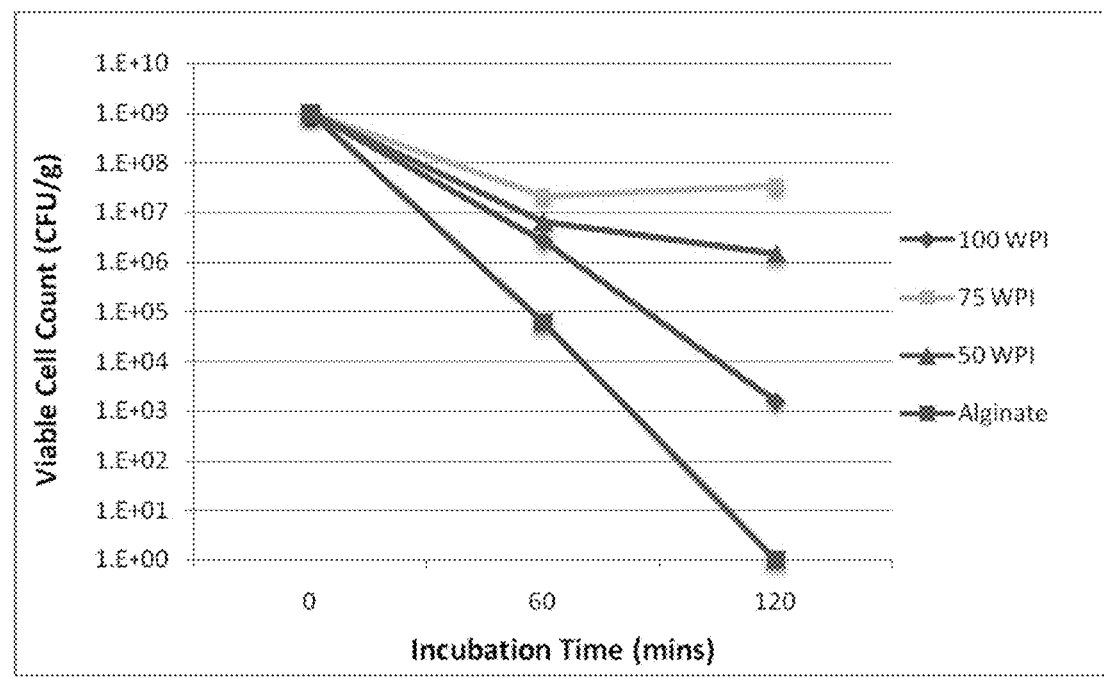
FIG. 8 depicts a graph of viable cell counts of microencapsulated *L. acidophilus* cells following incubation in simulated gastric fluid and pepsin for 120 minutes.

As shown in FIG. 8, the viable cell counts of *L. acidophilus* contained within WPI capsules or alginate capsules in simulated gastric fluid with pepsin (pH 2.0±0.1) were noticeably lower after 120 minutes than within WPI-alginate capsules. More particularly, capsules consisting of 75:25 and 50:50 (WPI:alginate) were the most stable capsules in SGF. According to aspects of the invention, the decrease of viable probiotic bacteria in the inventive capsules upon subjection to pH 2.0 fluid for up to 120 minutes comprises 0 to $1.0 \times 10^3$ CFU/gram capsules.

Chen and Subirade (2007), who investigated the release of riboflavin from WPI capsules and alginate capsules, suggested that the more rapid release of riboflavin from WPI capsules and alginate capsules was due to direct diffusion from the simpler internal structures as compared to the more complex structure of WPI/alginate capsules prepared from water-in-oil emulsions. In addition, the literature indicates that alginate may form a protective layer over the WPI capsule as a result of the interaction between WPI and alginate. A transacylation chemical reaction between protein and alginate (Chen et al., 2006) involves the formation of amide bonds between protein and alginate upon addition of an alkalizing agent (e.g., sodium hydroxide) to the capsules, and resulted in a membrane forming on the capsule surface. Such a membrane may protect the capsule from degradation from environmental stresses, for instance pH and pepsin activity.

Alginate capsules were the least stable in simulated gastric fluid with no detectable viable cells (<$10^1$ CFU/g) after 120 minutes incubation, as shown in FIG. 8. As discussed, previous studies have shown alginate capsules to be relatively stable in gastric fluids, and therefore the low cell count is likely a result of the porous structure of the capsules allowing entry of SGF into the capsule during incubation. As a result of the porosity, the surface area exposed to the SGF may have been significant enough to allow the bacteria to be released to the surrounding medium. Chandramouli et al. (2004) reported the complete release of *L. acidophilus* CSCC 2400 bacteria from 1% alginate capsules within 10 minutes of incubation in SGF.

Viability of Microencapsulated and Free Cells under Heat Treatment

Figure 9:
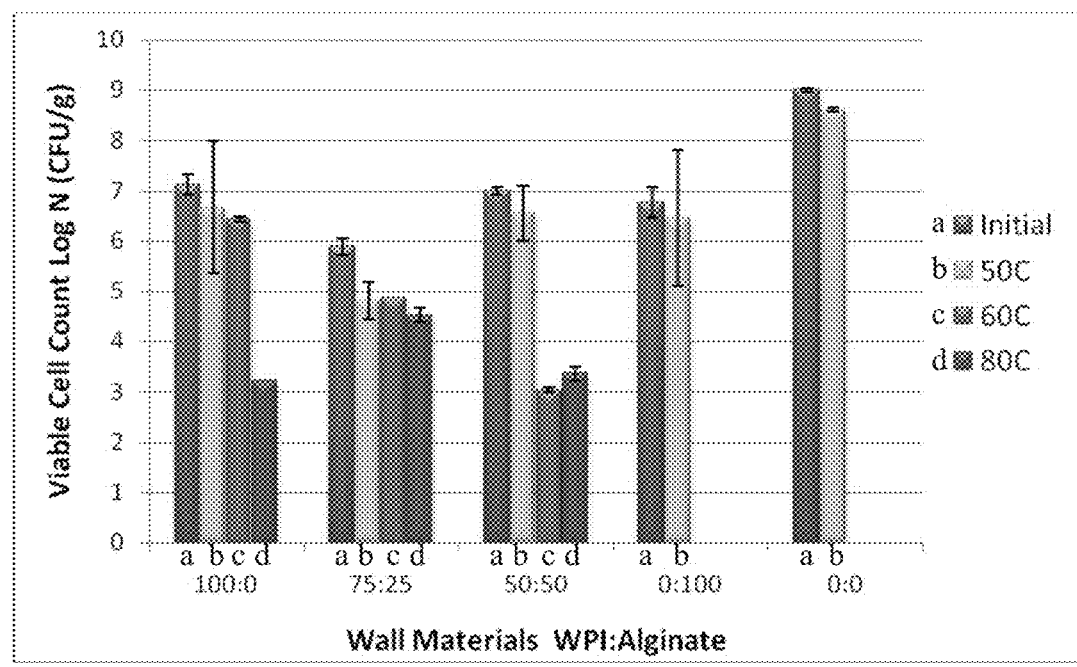
FIG. 9 depicts a graph of viable cell counts of free and encapsulated *L. acidophilus* cells following incubation in distilled water at 37, 50, 60 or 80 degrees Celsius.

Free and encapsulated *L. acidophilus* cells were incubated at 37° C., 50° C., 60° C. and 80° C. for 20 minutes in distilled water (pH 7.0). As shown in FIG. 9, a small but significant decrease in viable cell counts of free *L. acidophilus* cells was observed from incubation at 37° C. to 50° C. as cell counts dropped from Log 9.00 to Log 8.61 CFU/g. Viable cell counts were dramatically reduced to non-detectable levels following incubation at 60° C. and 80° C., suggesting that 60° C. is lethal for *L. acidophilus*. These results agree with what is generally known about *L. acidophilus* and results reported in the literature. Reinheimer et al. (1995) reported that proteolytic and acidifying activities of *L. acidophilus* were high at 37° C. and 40° C., yet fell to negligible activities when cells were treated at 55° C.

The viable cell count for WPI capsules was log 7.11, 6.67, 6.43 and 3.20 CFU/g following incubation at 37° C., 50° C., 60° C. and 80° C., respectively. FIG. 9 shows that no significant differences in viable cell counts were observed between 37° C., 50° C. and 60° C., suggesting that WPI capsules protected bacteria from thermal damage up to 60° C. After incubation at 80° C. for 20 minutes, however, approximately a 3 log reduction was observed in viable bacteria cell numbers. For 75:25 WPI:alginate capsules, viable bacteria cell counts decreased significantly from log 5.89 to log 4.81 CFU/g after incubation for 20 minutes at 50° C., as shown in FIG. 9. At each incubation temperature of 50° C., 60° C. and 80° C., the capsules appeared to protect bacteria from thermal damage as evidenced by no significant changes in viable cell count observed between the three temperatures: the viable cell counts for 50° C., 60° C. and 80° C. were log 4.81, 4.88 and 4.53 CFU/g, respectively.

According to aspects of the invention, the decrease of viable probiotic bacteria in the inventive capsules upon subjection to a temperature of up to 50° C. for up to 20 minutes in a pH 7.0 solution comprises 0 to 50 CFU/gram capsules. Similarly, the decrease of viable probiotic bacteria in inventive capsules upon subjection to a temperature of up to 60° C. for up to 20 minutes in a pH 7.0 solution comprises 0 to $1 \times 10^4$ CFU/gram capsules, preferably 0 to $1 \times 10^2$ CFU/gram capsules. The decrease of viable probiotic bacteria in inventive capsules upon subjection to a temperature of up to 80° C. for up to 20 minutes in a pH 7.0 solution comprises 0 to $1 \times 10^4$ CFU/gram capsules, preferably 0 to $1 \times 10^3$ CFU/gram capsules.

Again referring to FIG. 9, no significant difference in viable cell counts was observed between incubation at 37° C. and 50° C. for *L. acidophilus* encapsulated in alginate capsules, with cell counts of log 6.76 and log 6.46 CFU/g being observed. However, at 60° C. and 80° C. no colony forming units were detected, suggesting that no thermal protection was offered by alginate capsules above 50° C. Whey-protein containing capsules exhibited a thermal protective effect on the viability of L. acidophilus cells more than free and alginate encapsulated cells. Surprisingly, WPI containing capsules provided thermal protection to bacteria cells even up to 80° C., with WPI capsules, 75:25 WPI:alginate capsules and 50:50 WPI:alginate capsules producing log reductions of 4, 2 and 4, CFU/g respectively. Therefore, 75:25 WPI:alginate capsules were the most effective at providing a thermal barrier to encapsulated bacteria.

These experiments demonstrate the ability of encapsulated probiotic bacteria to survive thermal and gastrointestinal conditions. Viable cell numbers of non-encapsulated probiotic bacteria readily decreased in harsh environmental conditions, such as gastric and thermal conditions, illustrating their sensitivity to acid and thermal stress. In contrast to free cells, capsules comprising WPI and alginate in combinations of 75:25 WPI:alginate and 50:50 WPI:alginate exhibited a protective effect on L. acidophilus cells at temperatures up to 80° C. Moreover, under gastric conditions, these capsules exhibited significant protection of bacteria, with 50:50 WPI:alginate capsules providing the most protection.

Example 8

The stability of encapsulated commercial probiotics under heat treatment in acid conditions was investigated in this Example. Increased interest in probiotic bacteria has led to industries focusing on incorporating probiotics in various food systems. Studies indicated, however, that bacteria may not survive in sufficient numbers when incorporated into foods. Consequently, providing probiotics with a physical barrier against harsh environmental conditions during the processing of commercial food production is receiving considerable interest (Kailasapathy, 2002). To date, little research has been carried out with an aim to incorporate probiotics into heat-treated acid foods like fruit juice.

When various foods containing probiotics are developed, several factors including titratable acidity, pH, hydrogen peroxide, dissolved oxygen content, storage temperature, and species and strains of microorganisms may affect the viability of probiotics (Anal and Singh, 2007). As described previously, encapsulating probiotic bacteria in WPI-alginate beads developed in this study could improve the viability of L. acidophilus ATCC 4356 against the harsh conditions like SGF or high heat treatment.

Bacterial Strains and Culture Condition

The bacteria strains used in this study were Lactobacillus casei and Bifidobacterium lactis HN019 (Howaru), which were provided by Christian Hansen (Denmark) and Danisco (USA), respectively. Bacteria were grown in Lactobacillus MRS broth (Difco Laboratories, Detroit, Mich.) at 37° C. for 24 hours under anaerobic conditions (GasPak EZ anaerobe container system, Becton, Dickinson and Company, USA). Prior to use in the experiments, bacteria were subcultured at least three times. The numbers of CFU were determined by the plate count method with culture of appropriate dilutions as described in Example 1.

Microencapsulation

Cells were propagated in two bottles containing 400 ml MRS broth for 24 hours at 37° C. under anaerobic condition, harvested by centrifugation at 8,500 rpm for 10 minutes at 4° C., and then suspended with 0.1% peptone water. The 75:25 WPI-Alginate capsules were aseptically prepared with cell suspension of one bottle, as described in Example 1 except that the WPI concentration was 10% (w/v). The other cell suspension was used for free cells as a control sample.

Survival of Free and Encapsulated Cells Tinder Heat Treatment in Acid Conditions Tolerance of encapsulated L. casei and B. lactis to heat treatment in acid conditions was determined by incubating an amount (1 gram or 1 milliliter) of 75:25 WPI:alginate capsules containing encapsulated bacteria cells, and free cells, in 9 ml of phosphate buffer (100 mM, pH 7.0) or citric acid buffer (10 mM, pH 3.5, 3.8 and 4.1) as a suspending medium. The conditions of treatment were as follows:
1) 60° C. for 5, 10 and 20 minutes at pH 7
2) 60° C. for 5 and 10 minutes at pH 3.5
3) 60, 70 and 80° C. for 5 minutes at pH 3.5
4) 65° C. for 5 minutes at pH 3.8 and pH 4.1
5) 92° C. for 4 seconds at pH 3.5

After these treatments, each sample was immediately cooled to room temperature and viable cells were enumerated as described in Example 1. For acid-treated encapsulated cells, the capsules were transferred into 9 ml phosphate buffer to be depolymerized and then digested using a stomacher for up to 30 minutes. One milliliter aliquots of the sample were then taken and viable cell counts were enumerated.

Figure 10A:
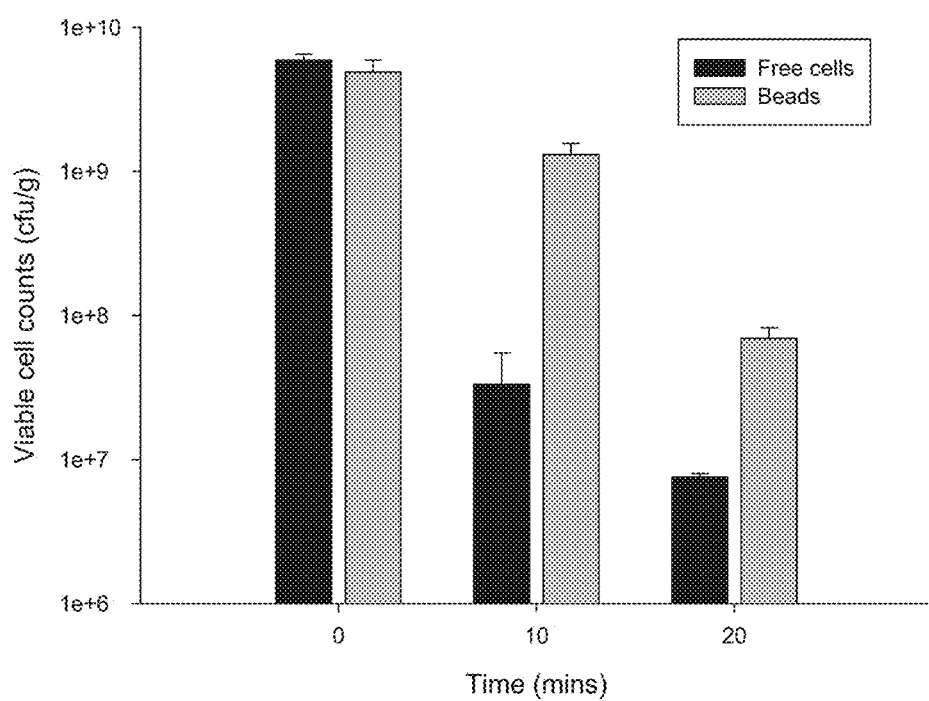
FIG. 10A depicts a graph of viable cell counts of free and encapsulated *L. acidophilus* cells following incubation in pH 7 phosphate buffer.
Figure 10B:
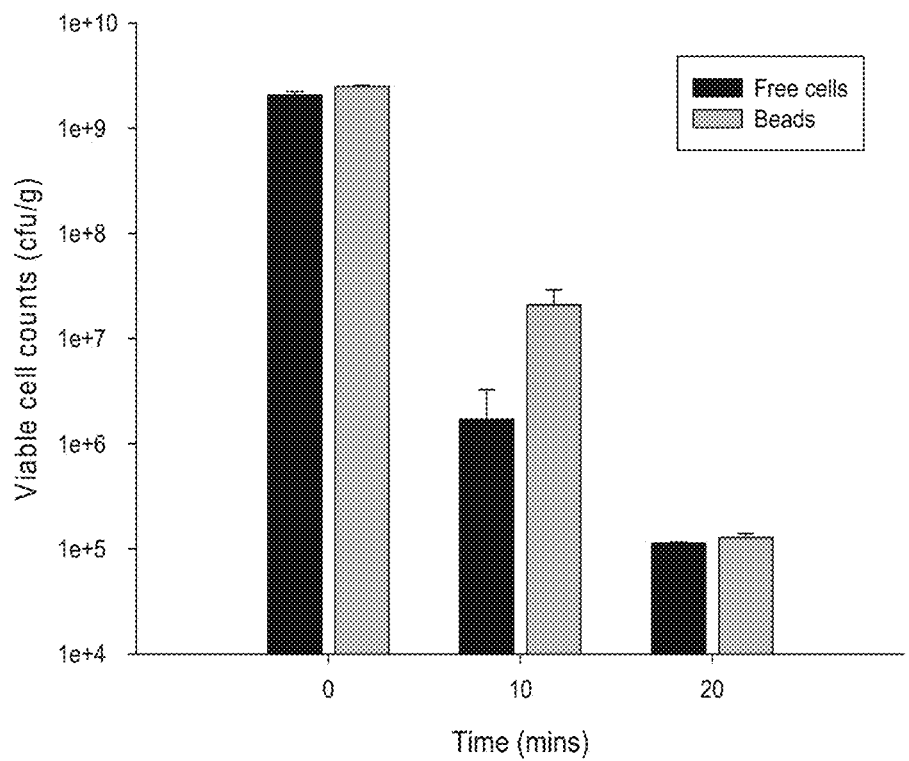
FIG. 10B depicts a graph of viable cell counts of free and encapsulated *Bifidobacterium lactis* cells following incubation in pH 7 phosphate buffer.

Referring to FIG. 10, free cells of L. casei (see FIG. 10A) and B. lactis (see FIG. 10B) in phosphate buffer (pH 7) were reduced about 2 and 3 log CFU/ml during heat treatment at 60° C. for 10 minutes, respectively. The survival of encapsulated cells of each strain was found to be higher than free cells, with a survival of about 1.5 log CFU/ml for L. casei and about 1 log CFU/ml for B. lactis. After 20 minutes of incubation at 60° C., the viability of encapsulated L. casei was about 1 log CFU/ml higher than free cells, but there was no difference between encapsulated and free cells for B. lactis. According to aspects of the invention, the decrease of viable probiotic bacteria in inventive capsules upon subjection to a temperature of up to 60° C. for up to 10 minutes in a pH 7.0 solution comprises 0 to $1\times10^3$ CFU/gram capsules, preferably 0 to $1\times10^2$ CFU/gram capsules. Similarly, the decrease of viable probiotic bacteria in inventive capsules upon subjection to a temperature of up to 60° C. for up to 20 minutes in a pH 7.0 solution comprises 0 to $1\times10^4$ CFU/gram capsules, preferably 0 to $1\times10^3$ CFU/gram capsules.

Figure 11:
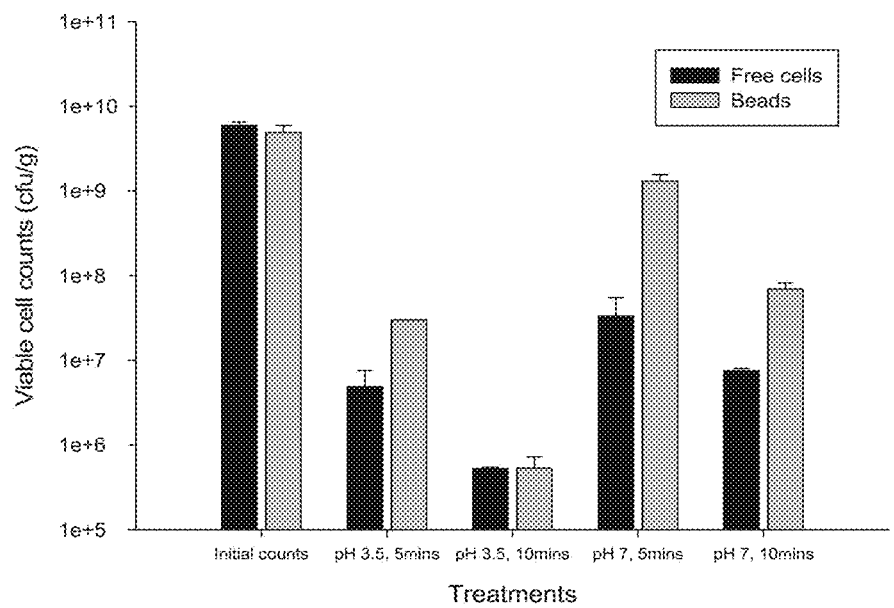
FIG. 11 depicts a graph of viable cell counts of free and encapsulated *L. casei* cells following heat treatment at 50 degrees Celsius.

Referring to FIG. 11, viable counts of free cells (L. casei) decreased, with about a 3 log reduction over heat treatment at 60° C. for 5 minutes when exposed to pH 3.5, while about 2 log reduction was observed in viable cells treated in neutral pH. This result illustrates that heating under acid pH condition may reduce the viability of microorganism as compared with neutral pH condition. Encapsulated cells of L. casei resulted in better survival (about 1 log CFU/ml higher) than for free cells under heat treatment at 60° C. for five minutes at low pH 3.5. Higher survival of encapsulated B. lactis under the same condition was also observed (data not shown). However, microencapsulation did not protect either type of microorganism after heat treatment for 10 minutes at pH 3.5. According to aspects of the invention, the decrease of viable probiotic bacteria in inventive capsules upon subjection to a temperature of up to 60° C. for up to 5 minutes in a pH 3.5 solution comprises 0 to $1\times10^2$ CFU/gram capsules. Similarly, the decrease of viable probiotic bacteria in inventive capsules upon subjection to a temperature of up to 60° C. for up to 10 minutes in a pH 3.5 solution comprises 0 to $1\times10^5$ CFU/gram capsules. In contrast, according to aspects of the invention the decrease of viable probiotic bacteria in inventive capsules upon subjection to a temperature of up to 60° C. for up to 5 minutes in a pH 7.0 solution comprises 0 to 50 CFU/gram capsules. Similarly, the decrease of viable probiotic bacteria in inventive capsules upon subjection to a temperature of up to 60° C. for up to 10 minutes in a pH 7.0 solution comprises 0 to $1 \times 10^2$ CFU/gram capsules.

Figure 12:
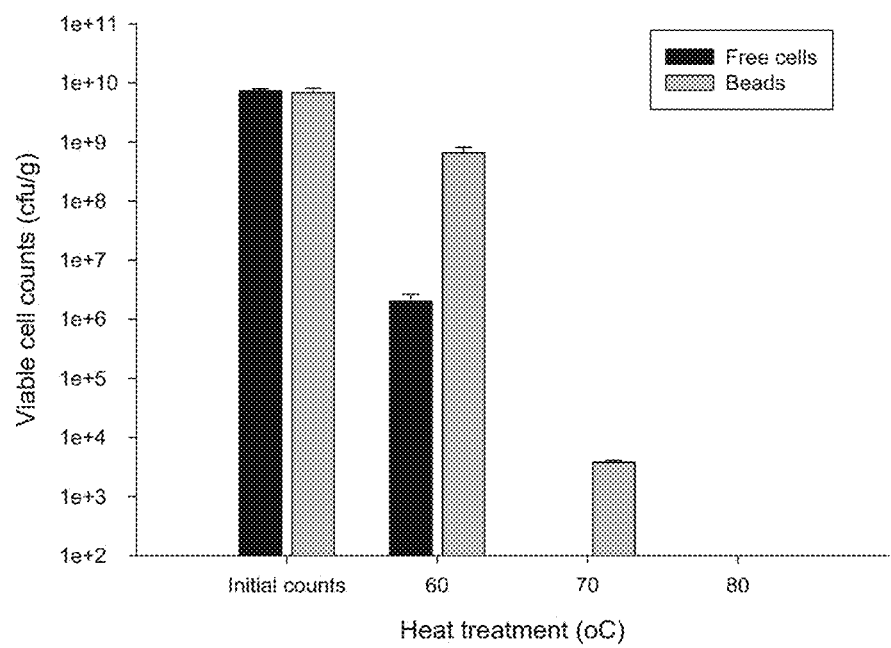
FIG. 12 depicts a graph of viable cell counts of free and encapsulated *L. casei* cells following heat treatment at 60, 70 and 80 degrees Celsius.

Referring to FIG. 12, when free and encapsulated cells of *L. casei* were exposed to temperatures of 70° C. and 80° C. for five minutes at pH 3.5, all of the free cells were killed, while as much as about log 3.5 of the encapsulated cells heated to 70° C. survived. This survival rate is very low for practical applications, however, because comestibles must contain at least $10^6$-$10^7$ CFU of viable probiotics for a food sold with probiotic health claims. According to aspects of the invention, the decrease of viable probiotic bacteria in inventive capsules upon subjection to a temperature of up to 70° C. for up to 5 minutes in a pH 3.5 solution comprises 0 to $1 \times 10^7$ CFU/gram capsules.

Figure 13A:
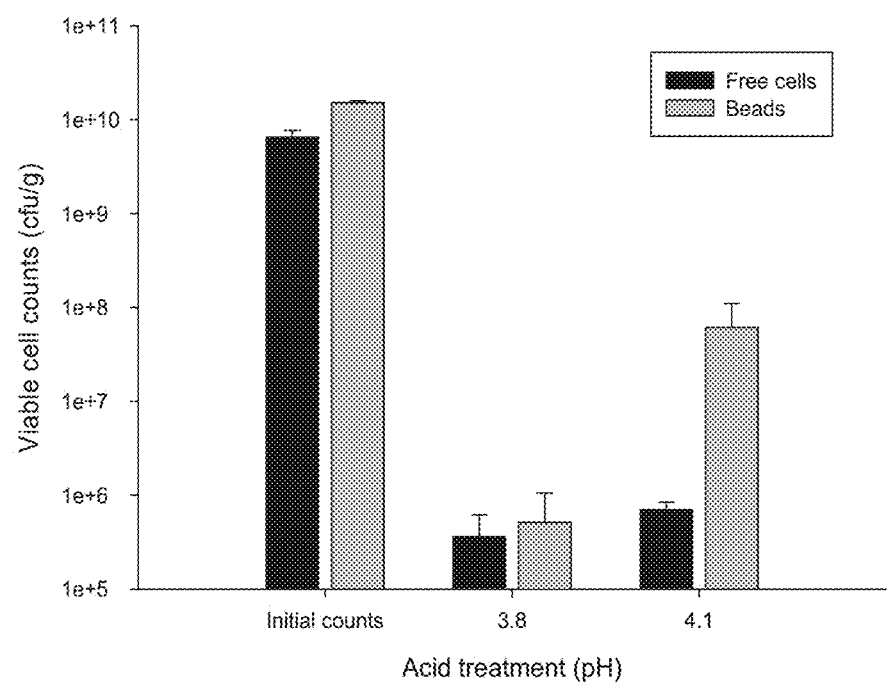
FIG. 13A depicts a graph of viable cell counts of free and encapsulated *L. casei* cells following acid treatment at pH 3.8 and 4.1.
Figure 13B:
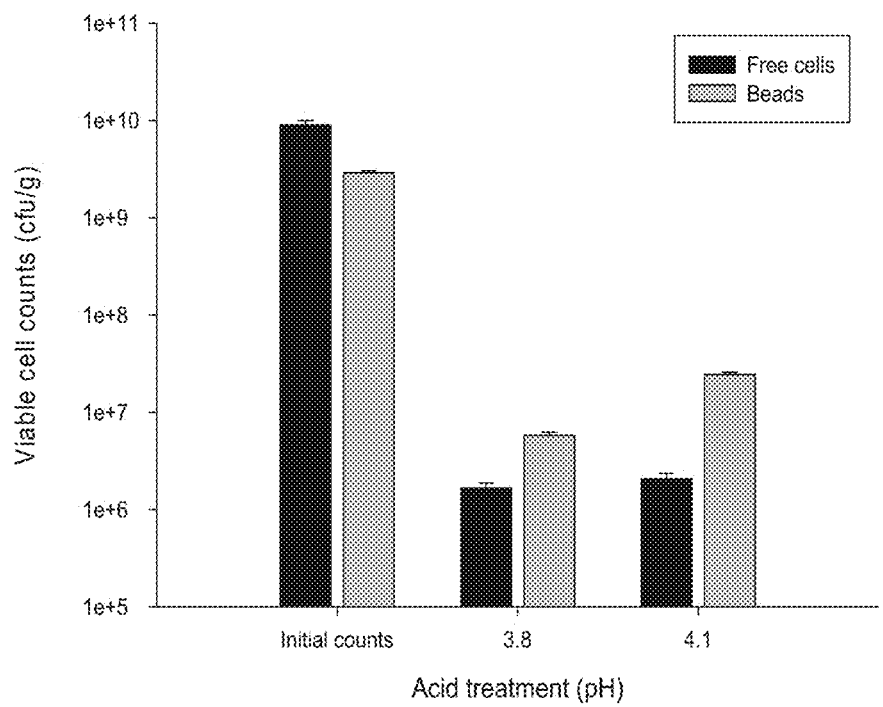
FIG. 13B depicts a graph of viable cell counts of free and encapsulated *Bifidobacterium lactis* cells following acid treatment at pH 3.8 and 4.1.

Referring to FIG. 13, when free and encapsulated *L. casei* cells were exposed to pH 3.8 at 65° C. for 5 minutes, no protective effect in viable count was observed in encapsulated cells (see FIG. 13A), but there was a protective effect of encapsulation on exposure to pH 4.1 and viable count of encapsulated cells was at least 1.5 log CFU/ml higher than free cells. For *B. lactis*, the viability of encapsulated cells was higher as compared with free cells even at pH 3.8 as well as at pH 4.1 (see FIG. 13B). At pH 4.1, compared to initial counts there was only about 2-log CFU/ml decrease in encapsulated cell numbers of *B. lactis* and about a 3.5 log CFU/ml reduction in the free cells. According to aspects of the invention, the decrease of viable probiotic bacteria in inventive capsules upon subjection to a temperature of up to 65° C. for up to 5 minutes in a pH 3.8 solution comprises 0 to $1 \times 10^5$ CFU/gram capsules, preferably 0 to $1 \times 10^3$ CFU/gram capsules. The decrease of viable probiotic bacteria in inventive capsules upon subjection to a temperature of up to 65° C. for up to 5 minutes in a pH 4.1 solution comprises 0 to $5 \times 10^2$ CFU/gram capsules.

The viability of encapsulated cells decreased proportionately with exposure to longer heating time. After 10 minutes of heat treatment, there was no difference between free and encapsulated cells (data not shown). No difference in viability between free and encapsulated cells of both strains was also observed on heat treatment at 65° C. for 5 minutes at pH 3.5 (data not shown).

Figure 14A:
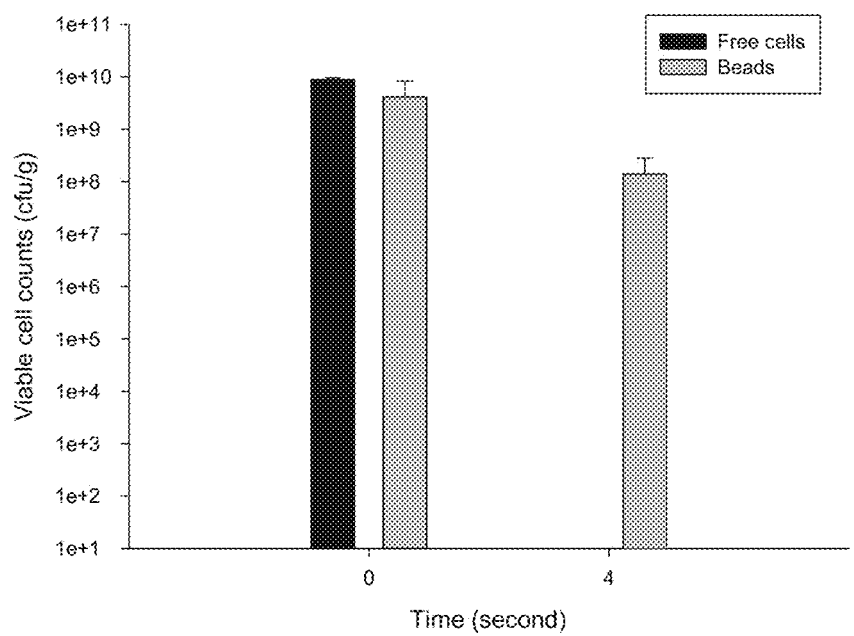
FIG. 14A depicts a graph of viable cell counts of free and encapsulated *L. casei* cells following heat treatment at 92 degrees Celsius for four seconds, at pH 3.5.
Figure 14B:
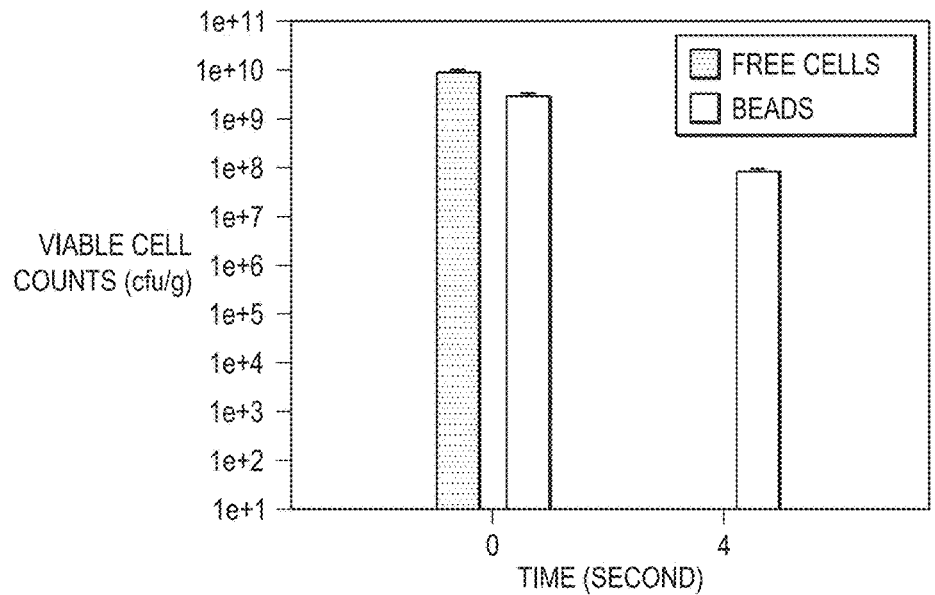
FIG. 14B depicts a graph of viable cell counts of free and encapsulated *Bifidobacterium lactis* cells following heat treatment at 92 degrees Celsius for four seconds, at pH 3.5.
Figure 15:
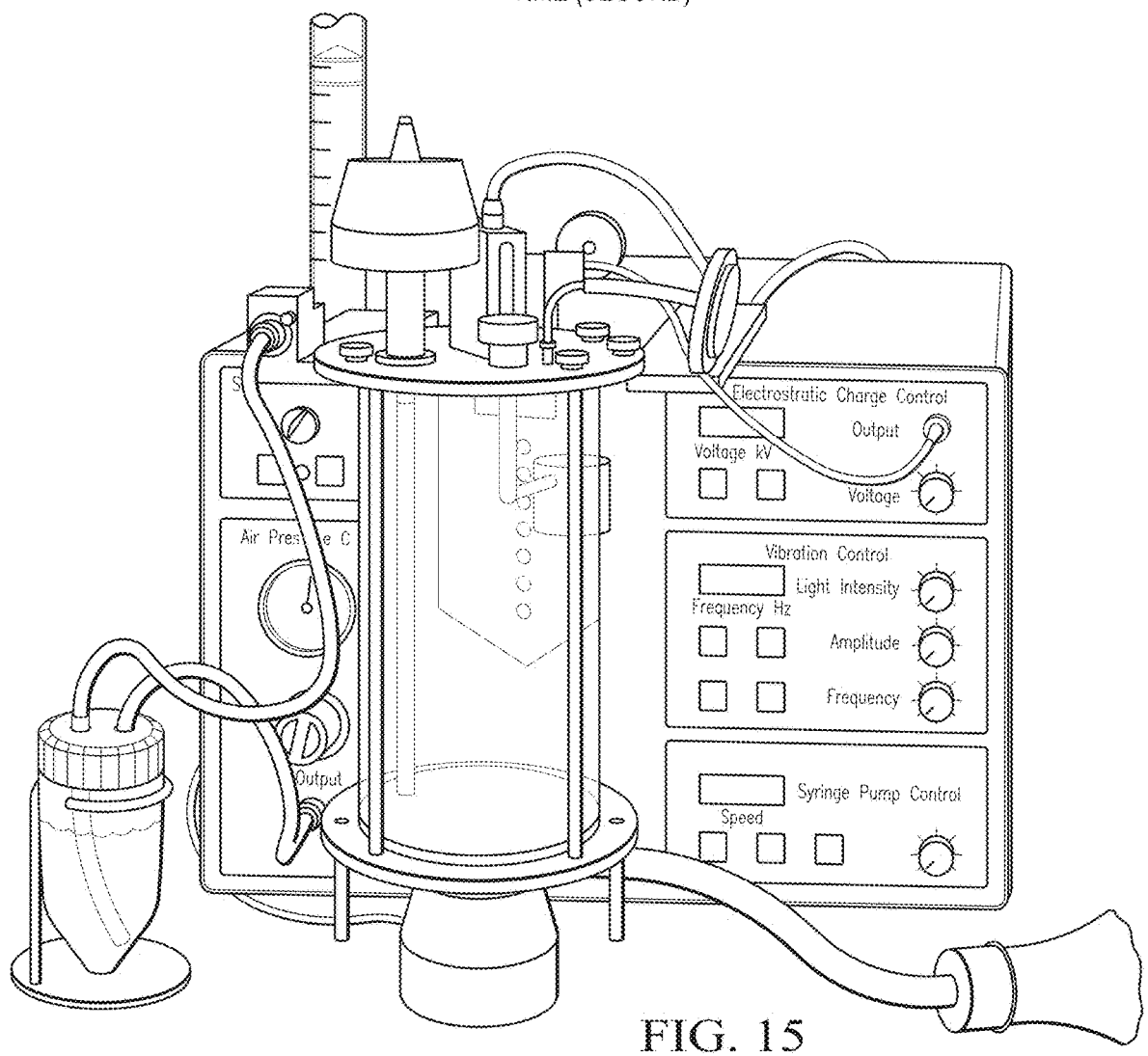
FIG. 15 depicts a photograph of an Inotech Encapsulator IE-50R.

Referring to FIG. 14, higher survival of encapsulated cells of both strains of *Lactobacillus casei* (see FIG. 14A) and *Bifidobacterium lactis* (Howaru) (see FIG. 14B) in acidic pH 3.5 at 92° C. for 4 seconds was observed, which shows that encapsulated cells may survive during commercial sterilization of low pH beverages. According to aspects of the invention, the decrease of viable probiotic bacteria in inventive capsules upon subjection to a temperature of up to 92° C. for up to 5 seconds in a pH 3.5 solution comprises 0 to $1 \times 10^2$ CFU/gram capsules.

The effect of capsule size on viability of bacteria was not investigated in this study but Chandramouli et al. (2004) showed the viability of encapsulated bacteria in simulated gastric conditions increased with increased capsule size (200-1000 um). Lee and Heo (2000) reported that survival of bacterial cells decreased with decreasing capsule size (diameters 1-2.6 mm). Sheu and Marshall (1993) indicated that larger bead diameters provided more protection for *Lactobacillus bulgaricus* in frozen desserts.

Food-grade microcapsules containing sensitive probiotics were developed in this study using a weight ratio of 75:25 of whey protein isolate and alginate, and proved to be efficient in increasing the viability of probiotic bacteria as compared to non-encapsulated free cells exposed to some heat treatments at low pH (i.e., 60° C. for 5 minutes at pH 3.5 and 65° C. for 5 minutes at pH 4.1), as well as a commercial sterilization condition of exposure to a temperature of 92° C. for 4 seconds.

Example 9

Incorporation of Encapsulated Probiotics into Commercial Fruit Juices

The consumption of foods and beverages containing probiotics appears to be a growing, global consumer trend (Verbeke, 2005). For instance, in Europe a large segment of the functional food market comprises foods fortified with probiotics. Commonly used bacteria for commercial probiotic applications include species of *Lactobacillus* and *Bifidobacterium* (Sheehan et al., 2007).

Beverages, such as fruit juices, that are consumed regularly and have an established market sector may represent an ideal delivery medium for probiotics. However, the development of functional juice fortified with probiotics can be dampened due to bacterial sensitivity to acidic conditions and particular components of juices. Typically, the minimum recommended level of viable probiotics which should be present in foods for any health benefits may be about $10^6$ CFU ml$^{-1}$ at the time of consumption (Boylston et al., 2004). Off-flavors caused by probiotic cultures in fruit juices might also cause consumers to dislike the product (Luckow and Delahunty, 2004). Microencapsulation is one technique that can be used to reduce the bacterial sensitivity and undesirable odors; however, there are some limitations, such as the size of microcapsule, if it is to be incorporated into a fruit juice. The size is preferably kept as small as possible to minimize the effects on sensory texture.

In this Example, *L. casei* and *B. lactis* Howaru were encapsulated using an Encapsulator (Inotech) apparatus and added into three kinds of commercial juices: orange juice, grape juice and cranberry juice. The viability of encapsulated and free cells in the juices was examined every two weeks for 10 weeks total storage time at an optimal temperature. The sensory tests were also carried out with orange juice and grape juice fortified with encapsulated cells.

Bacterial Strains, Culture Condition and Enumeration

The bacteria strains used in this study were *Lactobacillus casei* and *Bifidobacterium lactis* HN019 (Howaru), which were provided by Christian Hansen (Denmark) and Danisco (USA), respectively. The culture conditions and plate counting of bacteria were as described in Example 1.

Microencapsulation

Eight milliliters of fresh cells were propagated in 400 ml MRS broth for 24 hours at 37° C. under anaerobic conditions, harvested by centrifugation at 8,500 rpm for 10 minutes at 4° C. and then suspended with 0.1% peptone water. A 1% w/v sodium alginate and 10% WPI solutions were prepared as described in Example 1, except that the WPI and alginate mixture was diluted with autoclaved Milli-Q water to prevent the blocking of nozzle. The WPI-alginate capsules were aseptically prepared with a cell suspension in a 4%, w/v calcium chloride solution using an Encapsulator (IE-50R, Inotech, Switzerland) with a 300 μm nozzle. The vibration frequency was set at 1800 Hz, the electrostatic voltage was 1 kV, and the syringe pump speed was 320. The other cell suspension was used for free cells as a control sample. Capsules were hardened in calcium chloride solution for 30 minutes before being washed with Milli-Q water. The viable cells of capsules were then determined using the plate counting method.

Survival of Encapsulated Cells in Fruit Juices

Three kinds of commercial fruits juices were used, as shown in Table 3. Ten grams of encapsulated and free cells, respectively, were added to 500 mL of each juice. The viability of encapsulated and free cells in each juice was examined using the plate counting method every two weeks for 10 weeks of storage at the optimal temperature.

Particle Size Distribution

The microcapsules were analyzed for the volume weighted mean diameter in a Malvern Mastersizer 2000 Ver. 5.54 (Malvern Instruments Ltd., Malvern, UK) using laser diffraction technology.

TABLE 3

Commercial fruit juices

| Product name | Company | Key ingredients | Brix | pH | Acidity | Storage |
|---|---|---|---|---|---|---|
| McCoy Real Dark Grape Juice | Frucor Beverages Ltd., NZ | Reconstituted grape juice (100%), flavor, Vitamin C | 15.1 | 3.46 | 9.68 | Ambient |
| Ocean Spray Cranberry Classic | Ocean Spray International INC, Australia | Concentrated cranberry juice (25%), sugar, vitamin C | 11.9 | 2.73 | 16.50 | Ambient |
| Charlies Honest Juice Orange | Charlies Trading Company Ltd., Australia and NZ | Squeezed orange juice, vitamin C | 9.9 | 3.74 | 7.10 | Chilled |

Triangle Sensory Test

Ten grams of capsules per 500 mL were added to the grape and orange juices and tested by six trained sensory panelists. The amount (10 g) of microcapsules was the same as that of the microcapsules used for storage test. Two samples were plain juices and one sample was a microcapsule-containing juice.

The initial viable bacteria cell counts of each juice fortified with encapsulated and free cells of $L.$ $casei$ were about $6.44 \times 10^7$ CFU/ml and $1.29 \times 10^8$ CFU/ml, respectively (see Table 4). For $B.$ $lactis$ Howaru, the initial counts of each juice fortified with encapsulated and free cells were about $1.03 \times 10^8$ CFU/ml and $6.35 \times 10^7$ CFU/ml, respectively (see Table 5).

For McCoy grape juice fortified with $L.$ $casei$, although the cell count decreased in the juice with storage time, encapsulation of the bacteria cells provided some protective effect for probiotic bacteria. As shown in Table 4, the microcapsule-containing juice showed higher cell counts (i.e., 6.4 log CFU/ml) than free cell containing juice (i.e., 5.1 log CFU/ml) after 10 weeks storage. However, for $B.$ $lactis$ Howaru, the viability suddenly decreased up to about 1 log CFU in both types of juices after 6 week storage (see Table 5). According to aspects of the invention, the decrease of viable probiotic bacteria in inventive capsules upon subjection to storage at ambient temperatures (e.g., about 22-25° C.) for up to 8 weeks in a pH 3.5 grape juice comprises 0 to $1 \times 10^2$ CFU/gram capsules.

Cranberry juice has a lower pH and higher acidity as compared to the other juices and few of the free cells of $L.$ $casei$ and $B.$ $lactis$ Howaru survived, even after only two weeks of storage. The viability of microcapsules also showed a gradual decrease. Encapsulated $B.$ $lactis$ Howaru (see Table 5) was found to be more sensitive to this juice as compared to the encapsulated $L.$ $casei$ strain (see Table 4). According to aspects of the invention, the decrease of viable probiotic bacteria in inventive capsules upon subjection to storage at ambient temperatures (e.g., about 22-25° C.) for up to 2 weeks in a pH 2.75 cranberry juice comprises 0 to $1 \times 10^2$ CFU/gram capsules.

For chilled orange juice fortified with $L.$ $casei$, encapsulated and free cells gradually decreased, yet still maintained viability above 5.1 log CFU/ml after 10 weeks of storage (see Table 4). The viable cell count of microcapsules containing juice appears to be less than free cell containing juice; however, this difference was just due to difficulty in counting the cells because of presence of orange pulp. In contrast, for $B.$ $lactis$ Howaru, the viability in both juices was not maintained, similar to the results of the cranberry juice (see Table 5). According to aspects of the invention, the decrease of viable probiotic bacteria in inventive capsules upon subjection to storage at ambient temperatures of 25° F. (1.67° C.) for up to 10 weeks in a pH 3.75 orange juice comprises 0 to $1 \times 10^3$ CFU/gram capsules, preferably 0 to $1 \times 10^2$ CFU/gram capsules.

Sensory tests with orange juice demonstrated that five of the six trained sensory panelists did not detect a difference between the two kinds of juice, either containing capsules or not, possibly due to the presence of orange pulp. Moreover, the one person who detected the difference could not detect a different mouthfeel. It is generally estimated that a particle size above 1000 μm in diameter causes coarseness in tongue, but is not detectable below 3 μm size. The average size of microcapsules used in this Example was found to be about 490 μm. In sensory tests with grape juice, three of six trained sensory panelists detecting the microcapsules and felt some little lumps or grittiness but they did not detect any unpleasant taste.

TABLE 4

Numbers ($\log_{10}$/ml juice) of encapsulated and free cells ($L.$ $casei$) in three kinds of commercial juice over 10 weeks of storage at optimal temperature

| Storage weeks | Grape juice | | Cranberry juice | | Orange juice | |
|---|---|---|---|---|---|---|
| | Free cell | Bead | Free cell | Bead | Free cell | Bead |
| 0 | 8.1 | 7.8 | 8.1 | 7.8 | 8.1 | 7.8 |
| 2 | 7.7 | 7.6 | <4* | 6.2 | 7.1 | 5.4 |
| 4 | 6.7 | 7.3 | 0 | 3.2 | 6.7 | 6.3 |
| 6 | 6.1 | 7.1 | 0 | 1 | 6.1 | 5.7 |
| 8 | 5.5 | 6.9 | 0 | 0.5 | 6.0 | 6.0 |
| 10 | 5.1 | 6.4 | 0 | 0.5 | 5.3 | 5.1 |

*ND, out of dilution range

TABLE 5

Numbers ($\log_{10}$/ml juice) of encapsulated and free cells ($B.$ $lactis$ Howaru) in three kinds of commercial juice over 8 weeks of storage at optimal temperature.

| Storage weeks | Grape juice | | Cranberry juice | | Orange juice | |
|---|---|---|---|---|---|---|
| | Free cell | Bead | Free cell | Bead | Free cell | Bead |
| 0 | 7.8 | 8.0 | 7.8 | 8.0 | 7.8 | 8.0 |
| 2 | 6.7 | 6.8 | 0 | <2.4* | <3* | 4.1 |
| 4 | 5.1 | 5.6 | 0 | 0.6 | 0 | 0.4 |
| 6 | <1* | <1.3* | 0 | 0.5 | 0 | <1* |
| 8 | — | — | — | — | — | — |

*ND, out of dilution range

As shown in Table 4, in grape juice fortified with *L. casei*, the encapsulation provided a protective effect. In orange juice, the viability of encapsulated and free cells of *L. casei* was found to be maintained at around 5.1 log CFU/ml after 10 weeks of storage, possibly due to the low storage temperature and low acidity.

The volume weighted mean diameter of the capsules was found to be about 490 μm. Sensory tests indicated that consumers may not feel any difference in orange juice fortified with microcapsules, potentially due to the presence of pulp in orange juice. Although the presence of microcapsules in grape juice could be detected, the microcapsules might not provide any unpleasant taste or mouthfeel.

Those of ordinary skill in the art will understand that, for convenience, some ingredients are described here in certain cases by reference to the original form of the ingredient in which it is added to the beverage products, formulations and methods disclosed here. Such original form may differ from the form in which the ingredient is found in the finished beverage product or formulation. Thus, for example, sucrose and liquid sucrose would typically be substantially homogenously dissolved and dispersed in a solution. Likewise, other ingredients identified as a solid, concentrate (e.g., juice concentrate), etc. would typically be homogenously dispersed throughout the composition, rather than remaining in their original form. Thus, reference to the form of an ingredient of a product or formulation should not be taken as a limitation on the form of the ingredient in the product of formulation, but rather as a convenient means of describing the ingredient as an isolated component of the comestible product or formulation.

Given the benefit of the above disclosure and description of exemplary embodiments, it will be apparent to those skilled in the art that numerous alternative and different embodiments are possible in keeping with the general principles of the invention disclosed here. Those skilled in this art will recognize that all such various modifications and alternative embodiments are within the true scope and spirit of the invention. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc.

What is claimed:

1. A food product comprising:
a plurality of capsules comprising a gelled mixture of (i) substantially chemically unreacted alginate selected from a group consisting of sodium alginate and potassium alginate, (ii) denatured whey protein isolate, and (iii) $1.0 \times 10^9$-$1.0 \times 10^{12}$ colony forming units (CFU) of probiotic bacteria cells per gram of the capsules;
wherein the weight ratio of the whey protein isolate to the alginate is between 1:1 and 9:1;
wherein the capsules have an average particle size of between 1 micron and 1000 microns (μm) in diameter; and
wherein each of the plurality of capsules has an outer shell and an interior material comprising the same biopolymers, and wherein the outer shell has a denser polymerization than the interior material.

2. The food product of claim 1, wherein the food product is a beverage, and wherein the beverage further comprises:
at least one aqueous liquid; and
between 0.1 grams and 3 grams of the plurality of capsules per fluid ounce of the beverage.

3. The beverage of claim 2, wherein the weight ratio of the whey protein to the alginate is from 1:1 to 4:1.

4. The beverage of claim 2, wherein the at least one aqueous liquid consists essentially of fruit juice or vegetable juice.

5. The beverage of claim 2, wherein the at least one aqueous liquid comprises a fruit juice selected from the group consisting of orange juice, cranberry juice, grape juice, pineapple juice, apple juice, mango juice, coconut juice, and a combination of any of them.

6. The beverage of claim 2, wherein the average particle size of the capsules is less than 500 microns in diameter.

7. The beverage of claim 2, further comprising a vegetable component.

8. The beverage of claim 2, further comprising a natural non-nutritive sweetener selected from the group consisting of a rebaudioside, a steviol glycoside, *Stevia rebaudiana* extract, Lo Han Guo, mogroside V, monatin, glycyrrhizin, thaumatin, monellin, brazzein, and mixtures of any of them.

9. The beverage of claim 8, wherein the natural non-nutritive sweetener is selected from the group consisting of rebaudioside A, rebaudioside B, rebaudioside C, rebaudioside D, rebaudioside E, steviolbioside, dulcoside A, and a combination thereof.

10. The beverage of claim 2, wherein the plurality of capsules comprise beads.

11. The beverage of claim 2, wherein the probiotic bacteria comprises *Bifidobacterium* spp., *Lactobacillus* spp., or mixtures thereof.

12. The beverage of claim 2, wherein the beverage comprises viable probiotic bacteria in an amount of at least $1.0 \times 10^6$ CFU/gram capsules when the beverage product is stored at a temperature of 22-25° C. for at least two weeks.

13. The food product of claim 1, wherein the weight ratio of the whey protein to the alginate is from 1:1 to 3:1.

14. The beverage of claim 2, further comprising at least one additional ingredient selected from the group consisting of taste modifiers, organic acids, flavorants, vitamins, minerals, buffering agents, colorants, and mixtures of any of them.

15. The beverage of claim 14, wherein the additional ingredient is at least one organic acid selected from the group consisting of citric acid, malic acid, ascorbic acid, tartaric acid, lactic acid, and mixtures of any of them.

16. The beverage of claim 14, wherein the additional ingredient is at least one mineral selected from the group consisting of calcium, magnesium, and mixtures thereof.

17. The beverage of claim 14, wherein the additional ingredient is vitamin D.

* * * * *